United States Patent
Van Keuren-Jensen

(10) Patent No.: US 10,168,340 B2
(45) Date of Patent: Jan. 1, 2019

(54) METHODS FOR THE DIAGNOSIS OF AMYOTROPHIC LATERAL SCLEROSIS

(71) Applicant: The Translational Genomics Research Institute, Phoenix, AZ (US)

(72) Inventor: Kendall Van Keuren-Jensen, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 305 days.

(21) Appl. No.: 14/776,347

(22) PCT Filed: Mar. 15, 2014

(86) PCT No.: PCT/US2014/030088
§ 371 (c)(1),
(2) Date: Sep. 14, 2015

(87) PCT Pub. No.: WO2014/145347
PCT Pub. Date: Sep. 18, 2014

(65) Prior Publication Data
US 2016/0033535 A1 Feb. 4, 2016

Related U.S. Application Data

(60) Provisional application No. 61/793,749, filed on Mar. 15, 2013.

(51) Int. Cl.
*C12Q 1/68* (2018.01)
*G01N 33/68* (2006.01)
*C12Q 1/6883* (2018.01)

(52) U.S. Cl.
CPC ....... *G01N 33/6896* (2013.01); *C12Q 1/6883* (2013.01); *C12Q 2600/112* (2013.01); *C12Q 2600/118* (2013.01); *C12Q 2600/158* (2013.01); *G01N 2800/28* (2013.01); *G01N 2800/2878* (2013.01); *G01N 2800/50* (2013.01); *G01N 2800/56* (2013.01)

(58) Field of Classification Search
None
See application file for complete search history.

(56) References Cited

U.S. PATENT DOCUMENTS

| 5,716,784 A | 2/1998 | Di Cesare |
| 2004/0053394 A1 | 3/2004 | Gururajan |
| 2010/0216130 A1 | 8/2010 | Stephan |

OTHER PUBLICATIONS

McLean, Jesse Ryan, Identification and Characterization of Peripherin Isoforms in Amyotrophic Lateral Sclerosis, PhD Thesis, University of Toronto, 2009, Abstract; Fig. 3.4v.
Cleveland, at al., From Charcot to Lou Gehrig: deciphering selection motor neuron death in ALS, Nat. Rev. Neuroscience, (2) 806-819 (2001).
Briujn, et al., Unraveling the mechanisms involved in motor neuron degeneration in ALS, Ann. Rev. Neuroscience, (1) 293-299 (2000).
Dunckley, et al., Whole-Genome Analysis of Sporadic Amyotrophic Lateral Sclerosis, New England Journal of Medicine, (358) 775-788 (2007).
Fernandez-Santiago, et al., No evidence of association of FLJ10986 and IPTR2 with ALS in a large German Cohort, Neurobiology of Aging, (32) 551e1-551e4 (2011).
Daoud, et al., Analysis of DPP6 and FGGY as candidate genes for amyotrophic lateral sclerosis, Amyotrophic Lateral Sclerosis and Frontotemporal Degeneration, (11) 389-391(2010).
Chio et al., A two-stage genome-wide association study of sporadic amyotrophic lateral sclerosis, Human Molecular Genetics, (18) 1524-1532 (2009).
Van Es, et al., Analysis of FGGY as a risk factor for sporadic amyotrophic lateral sclerosis, Amyotrophic Lateral Sclerosis and Frontotemporal Degeneration, (10) 441-447 (2009).
Fang, et al., Clinical and genetic features of patients with sporadic amyotrophic lateral sclerosis, Amyotrophic Lateral Sclerosis and Frontotemporal Degeneration, (10) 350-354 (2009).
Chamberlin, et al., New RNA Polymerase from *Escherichia coli* infected with Bacteriophage T7, Nature (228):227 (1970).
Wu, et al., The ligation amplification reaction (LAR)—amplification of specific DNA sequences using sequential rounds of template-dependent ligation, Genomics, 4(4):560-9, May 1989.

*Primary Examiner* — John D Ulm

(57) ABSTRACT

The present invention is directed to systems and methods for diagnosing amyotrophic lateral sclerosis (ALS) by assessing the expression level of a marker, FGGY. In other aspects, the present invention is also directed to systems and methods of establishing a prognosis of ALS disease severity by assessing the expression level of FGGY.

16 Claims, 10 Drawing Sheets
Specification includes a Sequence Listing.

METHODS FOR THE DIAGNOSIS OF AMYOTROPHIC LATERAL SCLEROSIS

CROSS-REFERENCE TO RELATED APPLICATIONS

The present application is the national stage of International Patent Application No. PCT/US2014/030088, filed on Mar. 15, 2014, which claims priority to U.S. Application No. 61/793,749, filed Mar. 15, 2013, the entire contents and disclosure of which are herein incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 21.4 kilobyte ASCII (text) file named "FGGYSeq_List" created on Sep. 14, 2015.

FIELD OF THE INVENTION

This application relates to systems and methods for the diagnosis of amyotrophic lateral sclerosis and more particularly, relates to the assessment of FGGY expression as a diagnostic marker for amyotrophic lateral sclerosis.

BACKGROUND OF THE INVENTION

Amyotrophic lateral sclerosis (ALS) is the most common motor neuron disease, with an incidence of one or two cases per 100,000 persons and a lifetime risk of one case per 800 persons. ALS is characterized by a progressive loss of motor neurons from the spinal cord, brain stem, and cerebral cortex, leading to paralysis and death within two to five years after diagnosis without intensive physiological support. Ten percent of ALS cases are familial forms resulting from highly penetrant, monogenic mutations that cause disease.

Little is known about the specific genes that contribute to the development of sporadic ALS. Despite the extensive study of familial ALS, including the creation of animal models, the key events in the initiation and progression of sporadic ALS remain relatively unclear. Pathologically, sporadic ALS is characterized by a loss of motor neurons from the motor cortex, brain stem, and ventral horns of the spinal cord. In addition, ubiquitinated inclusions (i.e., covalent bonds between ubiquitin and other proteins that mark the other proteins for degradation) have been observed in the lower motor neurons, although the role of the inclusions in the initiation and progression of the disease remains unclear. To date, numerous mechanisms have been implicated in the selective degradation of motor neurons in patients with sporadic ALS, including oxidative damage, excitotoxicity, apoptosis, cytoskeletal dysfunction, axonal-transport defects, inflammation, protein processing and degradation defects, mitochondrial dysfunction. See Cleveland, D. W. and Rothstein J. D., *From Charcot to Lou Gherig: deciphering selection motor neuron death in ALS*, Nat. Rev. Neuroscience (2) 806-819 (2001); and L. I. Pasinelli et al., *Unraveling the mechanisms involved in motor neuron degeneration in ALS*, Ann. Rev. Neuroscience (1) 293-299 (2000).

In addition to the relatively unknown mechanisms and initiation events linked to both sporadic and familial ALS, there are only limited treatment options. To date, there is only one Food and Drug Administration-approved pharmaceutical for the treatment of ALS, Riluzole. However, this drug only extends life by an average of three months and does not significantly improve the quality of life.

FGGY or FLJ10986 was previously reported to be generally associated with ALS in 2007. T. Dunckley et al., *Whole-Genome Analysis of Sporadic Amyotrophic Lateral Sclerosis*, New England Journal of Medicine (358) 775-788 (2007). However, this study's analysis showed no significant normalized differences in FGGY protein expression in spinal-cord samples in ALS patients compared to non-ALS control samples and mixed FGGY protein expression levels in other tissue samples (i.e., kidney, liver, lung, head, brain, and cerebrospinal fluid). Other studies have shown a mixture of potentially relevant associations between FGGY and sporadic ALS and no relevant and/or significant relationships between this disease and gene. See R. Fernandez-Santiago et al., *No evidence of association of FLJ10986 and IPTR2 with ALS in a large German Cohort*, Neurobiology of Aging (32) 551e1-551e4 (2011); H. Daoud et al., *Analysis of DPP6 and FGGY as candidate genes for amyotrophic lateral sclerosis*, Amyotrophic Lateral Sclerosis and Frontotemporal Degeneration (11) 389-391 (2010); A. Chio et al., *A two-stage genome-wide association study of sporadic amyotrophic lateral sclerosis*, Human Molecular Genetics (18) 1524-1532 (2009); M. A. Van Es et al., *Analysis of FGGY as a risk factor for sporadic amyotrophic lateral sclerosis*, Amyotrophic Lateral Sclerosis and Frontotemporal Degeneration (10) 441-447 (2009); and D. Fang et al., *Clinical and genetic features of patients with sporadic amyotrophic lateral sclerosis*, Amyotrophic Lateral Sclerosis and Frontotemporal Degeneration (10) 350-354 (2009).

Taken together, there is a demonstrated need for an assessment of the FGGY contribution to ALS disease severity and progression to use this relationship to improve early diagnoses and prognoses of ALS.

The articles, treatises, patents, references, and published patent applications described above and herein are hereby incorporated by reference in their entirety for all purposes.

SUMMARY

Some embodiments of the invention provide a method of determining whether a subject is likely to have amyotrophic lateral sclerosis. In some aspects, the method includes receiving a sample from the subject and adding a reagent to a mixture comprising the sample. For example, the reagent is capable of binding to a marker comprising a sequence selected from the group consisting of SEQ ID NO. 1, SEQ ID NO. 2, SEQ ID NO. 3, SEQ ID NO. 4, SEQ ID NO. 5, and SEQ ID NO. 6. Thereafter, the method includes subjecting the mixture to conditions that allow detection of binding of the reagent to the sample and assessing the expression of the marker in the sample and in a control sample. In some aspects, assessing the expression level comprises determining a level of binding of the reagent to the marker in the sample and determining a level of binding to the marker in the control sample. Then, the method includes determining that subject is likely to have amyotrophic lateral sclerosis when the binding of the reagent to the marker in the sample is greater than the binding of the reagent to the control sample. In some aspects, the marker may comprise FGGY protein or FGGY mRNA or other nucleotides.

In some particular aspects of the invention, the subject may be a mammal. For example, the subject can be a human. Moreover, the sample may comprise a tissue sample from the subject. In some aspects, the tissue sample may be a muscle sample from a human being suspected of having amyotrophic lateral sclerosis. For example, the muscle sample may be a sample of the subject's gastrocnemius muscle. In some aspects, the reagent may be at least one of an oligonucleotide or an antibody that is capable of binding to a FGGY nucleotide sequence or a FGGY amino-acid sequence, respectively.

Some embodiments of the invention provide a method of characterizing disease severity in a subject with amyotrophic lateral sclerosis. In some aspects, the method includes receiving a tissue sample from the subject and adding a reagent to a mixture comprising the tissue sample. For example, the reagent is capable of binding to a marker comprising a sequence selected from the group consisting of SEQ ID NO. 1, SEQ ID NO. 2, SEQ ID NO. 3, SEQ ID NO. 4, SEQ ID NO. 5, and SEQ ID NO. 6. Thereafter, the method includes subjecting the mixture to conditions that allow detection of binding of the reagent to the sample and assessing the expression of the marker in the sample and the control sample. In some aspects, assessing the expression level comprises determining a level of binding of the reagent to the marker in the sample and determining a level of binding to the marker in the control sample. Then, the method includes characterizing the amyotrophic lateral sclerosis as severe in the subject when the binding of the reagent to the marker in the tissue sample is greater than the binding of the reagent to the control sample. In some aspects, the marker may comprise FGGY protein or FGGY mRNA or other nucleotides.

In some particular aspects of the invention, the tissue sample may comprise a muscle sample from the subject. In some aspects, the muscle sample may be a sample of the subject's gastrocnemius muscle. In some aspects, the reagent may be at least one oligonucleotide. In particular aspects, the method may further provide adding a second oligonucleotide to the mixture. In other aspects, the reagent may comprise an antibody. In some embodiments of the invention, the control sample is derived from a subject that does not have amyotrophic lateral sclerosis.

Some additional embodiments of the invention provide a method of determining whether a subject is likely to have amyotrophic lateral sclerosis. In these embodiments, the method includes receiving a muscle sample from a subject and adding a first antibody that is capable of binding to FGGY protein to a mixture comprising the muscle sample. Thereafter, the method includes subjecting the mixture to conditions that allow detection of binding to the first antibody to the FGGY protein and assessing the expression level of the FGGY protein in the muscle sample and a control muscle sample. In some aspects, assessing the expression level comprises determining a level of binding of the first antibody to the FGGY protein in the muscle sample and determining a level of binding of the first antibody to the FGGY protein in the control muscle sample. Then, the method includes determining that the subject is likely to have amyotrophic lateral sclerosis when the binding of the first antibody to the FGGY protein in the muscle sample is greater than the binding of the first antibody to the control muscle sample (e.g., a sample derived from a subject that does not have amyotrophic lateral sclerosis).

In some particular aspects of the invention, the subject may be a human and the muscle sample may comprise at least a portion of a gastrocnemius muscle from the subject. In some aspects, the method may further include adding a second antibody to the mixture. For example, the second antibody is capable of binding to the first antibody. In particular aspects of the invention, the method comprises a technique selected from the group consisting of flow cytometry, immunohistochemistry, enzyme-linked immunosorbent assay (ELISA), Western Blot, and immunoaffinity chromatography.

Additional objectives, advantages and novel features will be set forth in the description which follows or will become apparent to those skilled in the art upon examination of the drawings and detailed description which follows.

BRIEF DESCRIPTION OF THE DRAWINGS

In FIG. 9A, HEK293 cells were stained using DAPI and antibodies that detect FGGY and HnRNP C and the resulting images were merged. The merged image reflects the co-localization of HnRNP C and FGGY. In FIG. 9B, HEK293 cells were stained using DAPI and antibodies that detect FGGY and Fibrillarin, a nucleolar protein. The merged image (the only image presented in FIG. 9B) shows co-localization of FGGY and Fibrillarin. In FIG. 9C, HeLa cells were stained using DAPI and antibodies that detect FGGY and SMN1. The merged image (the only image presented in FIG. 9C) also shows co-localization of FGGY and SMN1.

Figure 1:
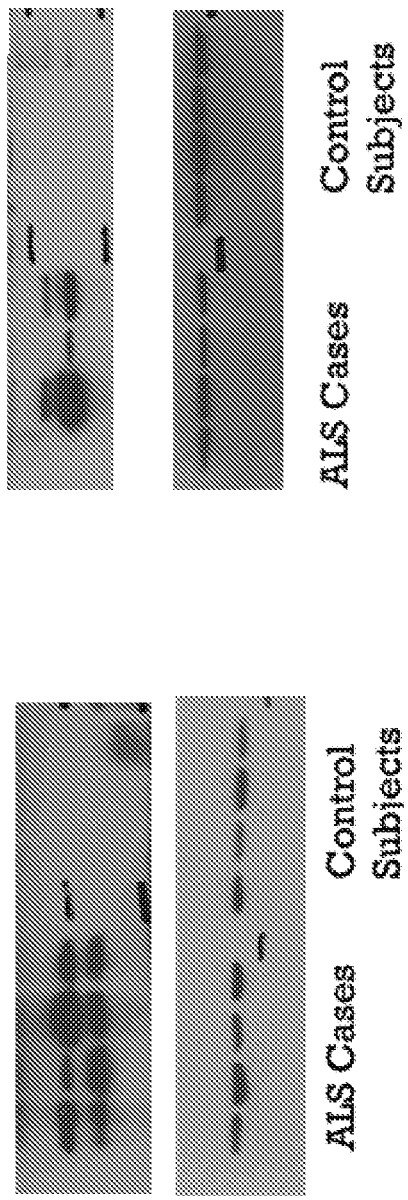
FIG. 1 is a set of Western Blots that indicate that FGGY protein expression significantly increases in muscle samples from ALS patients compared to muscle samples from non-ALS patients. In particular, seven out of eight ALS patients demonstrated higher FGGY protein expression. In the left Western Blot, the gastrocnemius muscle samples were from patients that were showing symptoms of ALS. In the right Western Blot, the gastrocnemius muscle samples were from postmortem procedures from persons who had ALS. As shown in both the right and the left Western Blots, FGGY protein levels were nearly undetectable in most control samples.

The headings used in the figures should not be interpreted to limit the scope of the claims.

DETAILED DESCRIPTION

The present invention is directed to systems and methods that can be used to diagnose one or more neuromuscular diseases. In some aspects, the present invention comprises systems and methods that can be used to diagnose amyotrophic lateral sclerosis (ALS) in a subject. In other aspects, the present invention comprises systems and methods that can be used to assess a prognosis of a subject with ALS or other neuromuscular disease. For example, the invention may comprise determining an expression level of a marker to make determinations regarding diagnoses and/or prognoses. In some aspects, the marker may comprise FGGY. In particular aspects, the marker may comprise at least a portion of the FGGY DNA, mRNA, and/or protein sequence that one skilled in the art can assess to determine a diagnosis and/or prognosis, as related to ALS.

Generally, some embodiments of the present invention can be used to identify a marker and/or used to assess the expression of the marker. A marker may be any molecular structure produced by a cell, expressed inside the cell, accessible on the cell surface, or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, or complementary sequences thereof. Alternatively, a marker may be represented by a protein sequence. The concept of a marker is not limited to the exact nucleic acid sequence or protein sequence or products thereof, rather it encompasses all molecules that may be detected by a method of assessing the marker. Without being limited by the theory, the detection of the marker may encompass the detection and/or determination of a change in copy number (e.g., copy number of a gene or other forms of nucleic acid) or in the detection of one or more translocations.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, underexpression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

The term "derived from" refers to the origin or source, and may include naturally occurring, recombinant, unpurified, or purified molecules. The proteins and molecules of the present invention may be derived from human or non-human molecules.

The term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably. In some particular aspects of the invention, FGGY comprises the nucleotide sequence of SEQ ID NO. 1. Moreover, FGGY comprises at least two isoforms that comprise the mRNA sequences of SEQ ID NO. 3 and SEQ ID NO. 5, respectively. As described herein, the reagents used to detect the presence and/or the expression levels of FGGY levels can detect each of SEQ ID NO. 1, SEQ ID NO. 3, and SEQ ID NO. 5. Any reference to the FGGY nucleotide sequence herein is to be construed as including all three isoforms.

The term "gene" refers to a nucleic acid or portion of a nucleic acid comprising a sequence that encodes a protein. It is understood in the art that a gene also comprises non-coding sequences, such as 5' and 3' flanking sequences (such as promoters, enhancers, repressors, and other regulatory sequences) as well as introns.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "polypeptide," "peptide," and "protein" are used interchangeably herein to refer to polymers of amino acids of any length. These terms also include proteins that are post-translationally modified through reactions that include glycosylation, acetylation and phosphorylation. In some particular aspects of the invention, FGGY protein comprises the amino acid sequence of SEQ ID NO. 2. Moreover, FGGY protein comprises at least two isoforms that comprise the amino acid sequences of SEQ ID NO. 4 and SEQ ID NO. 6, respectively. As described herein, the reagents used to detect the presence and/or the expression levels of FGGY protein levels can detect each of SEQ ID NO. 2, SEQ ID NO. 4, and SEQ ID NO. 6. Any reference to FGGY protein is to be construed to include all three FGGY protein isoforms.

The term "nucleotide" is defined as a modified or naturally occurring deoxyribonucleotide or ribonucleotide. Nucleotides typically include purines and pyrimidines, which include thymidine, cytidine, guanosine, adenine and undine.

The term "at least a portion" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

Determination of marker expression may be performed by one or more of the methods known to one of ordinary skill in the art. For example, gene expression levels may be determined by detection of (a) a polypeptide encoded by a marker gene, (b) mRNA encoding a marker protein or marker polypeptide, (c) a portion of DNA which constitutes a marker gene, or (d) any combination thereof.

For example, levels of marker expression can be detected by measuring levels of protein using specific binding compositions. The detection of protein levels may be carried out using any of the methods known to one of ordinary skill in the art including, but not limited to, chemiluminescence methods, histochemical staining or biochemical detection (i.e., immuno-histochemistry assays), Western Blot analysis, flow cytometry, immuno-precipitation (or the equivalent thereof for non-antibody agents), Plasmon resonance absorbance measurement, and the like. In one embodiment of the invention, the method of detecting protein levels is an immunoassay (such as an ELISA), which includes the use of at least one antibody. In yet another embodiment of the invention, protein staining, in tissue sample for example, formalin-fixed, paraffin-embedded tissue sections can be carried out by immuno-histochemistry using an antibody, and determining the expression of the gene.

For example, one embodiment of the invention is performed using an IHC kit which uses a primary mouse monoclonal antibody, a secondary anti-mouse IgG antibody, a peroxidase blocker to quench the endogenous peroxidase activity and a chromogenic substrate. Measurement of the polypeptide encoded by a marker may include measurements of fragments of the polypeptide, wherein the fragments arise from transcriptional or translational variants of the marker; or alternatively, differently sized polypeptides arise as a result of post translational modifications including proteolysis of a larger portion of a polypeptide.

Detection of levels of mRNA may also serve as an indicator of marker expression. The methods used to detect mRNA levels are well known in the art, and include the detection of hybridization or amplification with the mRNA encoding a gene product. This detection may be carried out by analysis of mRNA either in vitro or in situ (e.g., in a tissue sample) using one of the methods known to one of ordinary skill in the art as exemplified in the Current Protocols in Molecular Biology (John Wiley & Sons, 1999); in U.S. Pat. No. 5,882,864; and the like. An mRNA detected will be any RNA transcript of a specific gene, or fragment thereof.

Some embodiments of the invention may include assessing, determining, quantifying, or altering the expression of a marker. As used herein, expression encompasses any and all processes through which material derived from a nucleic acid template may be produced. Expression thus includes RNA transcription, mRNA splicing, protein translation, protein folding, post-translational modification, membrane transport, associations with other molecules, addition of carbohydrate moieties to proteins, phosphorylation, protein complex formation and any other process along a continuum that results in biological material derived from genetic material. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, microRNA silencing, small interfering RNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, or any other method of detecting a specific nucleic acid now known or yet to be disclosed. Other examples include any process of assessing expression that uses an antibody including the following nonlimiting examples, flow cytometry, immunohistochemistry, ELISA, Western blot, and immunoaffinity chromatography. Antibodies may be monoclonal, polyclonal, or any antibody fragment including an Fab, F(ab)2, Fv, scFv, phage display antibody, peptibody, multispecific ligand, or any other reagent with specific binding to a marker. Such methods also include direct methods used to assess protein expression including the following nonlimiting examples: HPLC, mass spectrometry, protein microarray analysis, PAGE analysis, isoelectric focusing, 2-D gel electrophoresis, and enzymatic assays. Samples from which expression may be detected include single cells, whole organs or any fraction of a whole organ, whether in vitro, ex vivo, in vivo, or post-mortem.

Other methods used to assess expression include the use of natural or artificial ligands capable of specifically binding one or more markers, including a protein, carbohydrate, fat, nucleic acid, catalytic site, or any combination of these such as an enzyme, glycoprotein, cell membrane, virus, cell, organ, organelle, or any uni- or multimolecular structure that constitutes a marker that may be specifically bound by a ligand. Such ligands include antibodies, antibody complexes, conjugates, natural ligands, small molecules, nanoparticles, or any other molecular entity capable of specific binding to a marker. Ligands may be associated with a label such as a radioactive isotope or chelate thereof, dye (fluorescent or nonfluorescent) stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, proapoptotic substances, pore forming substances, radioactive isotopes, or any other substance capable of killing a cell.

Positive expression encompasses any difference between a cell expressing markers and a cell that does not express one or more of the markers. The exact nature of positive expression varies by the method, but is well known to those skilled in the art of practicing a particular method. Positive expression may be assessed by a detector, an instrument containing a detector, or by aided or unaided human eye. Examples include but are not limited to specific staining of cells expressing a target in an IHC slide, binding of RNA from a sample to a microarray and detection of binding through the use of said microarray, a particular rate of dye incorporation in real-time RT-PCR measured in $\Delta Ct$ or alternatively in the number of PCR cycles necessary to reach a particular optical density at a wavelength at which a double stranded DNA binding dye (e.g., SYBR Green) incorporates, through release of label from a previously labeled reporter probe used in a real-time RTPCR reaction, detection of fluorescence on a cell expressing a target by a flow cytometer, the presence of radiolabeled bands on film in a Northern blot, detection of labeled blocked RNA by RNAse protection assay, cell death measured by apoptotic markers, cell death measured by shrinkage of a tumor, or any other signal for the expression of a marker in existence now or yet to be developed. In some aspects of the invention, positive expression is a sufficient level of expression to correlate with a particular state of ALS, such as disease severity.

In some aspects of the invention, reduced expression includes no detectable expression. However, the concept of reduced expression further encompasses insufficient expression to reach or exceed a threshold, cutoff, or level that has been previously shown to result in a particular cellular or physiological response. Reduced expression may include similar expression relative to a control that has been previously determined not to express the marker(s) or similar expression to a control that has been previously determined not to exhibit the response. In this case, even though expression may be detectable, it still constitutes reduced expression. In some aspects of the invention, an expression level of a marker in a control known to have a reduced or increase risk of recurrence is predetermined and expression similar to that level is correlated with reduced or increase risk of recurrence. Increased or reduced expression includes expression that is 75% 50%, 25%, 10%, 5%, 1%, 0.1%, greater or less of that of a control cell or a median level of expression in a population. Reduced expression may also include greater than or less than $1 \times 10^{-5}$ greater or less expression normalized to the expression of a housekeeping gene.

Assessing the risk of a particular disease outcome includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Some embodiments of the invention may comprise the use of one or more methods of amplifying a nucleic acid-based starting material (i.e., a template). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

An oligonucleotide may be any polynucleotide of at least 2 nucleotides. Oligonucleotides may be less than 10, 15, 20, 30, 40, 50, 75, 100, 200, or 500 nucleotides in length. While oligonucleotides are often linear, they may assume a circular or other two dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^{3}$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5((2-aminoethyl)-amino)naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Either primers or primers along with probes allow a quantification of the amount of specific template DNA present in the initial sample. In addition, RNA may be detected by PCR analysis by first creating a DNA template from RNA through a reverse transcriptase enzyme. The marker expression may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In one example of the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900 HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex Real Time-PCR/PCR can also be performed in other real-time PCR systems with multiplexing capabilities.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "template" refers to nucleic acid originating from a sample that is analyzed for the presence of a molecule of interest. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," and "amplification product" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification is often in reference to the quantity of a control sample. The control sample DNA may be co-amplified in the same tube in a multiplex assay or may be amplified in a separate tube. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in real time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject. Biological samples may also include sections of tissues such as biopsy and autopsy samples, and frozen sections taken for histologic purposes such as blood, plasma, serum, muscle, sputum, stool, tears, mucus, hair, skin, and the like. Biological samples also include explants and primary and/or transformed cell cultures derived from patient tissues. In some embodiments, the sample can comprise muscle tissue taken from a subject, including a living or a deceased subject.

The term "subject" is used in its broadest sense. In a preferred embodiment, the subject is a mammal. Non-limiting examples of mammals include humans, dogs, cats, horses, cows, sheep, goats, and pigs. Preferably, a subject includes any human or non-human mammal, including for example: a primate, cow, horse, pig, sheep, goat, dog, cat, or rodent, capable of developing ALS including human patients that are suspected of having ALS, that have been diagnosed with ALS, or that have a family history of ALS.

The present invention provides a kit to determine the levels of marker expression in the sample. Such a kit will comprise a reagent for detecting the mRNA encoding a marker, the corresponding polypeptide, or any combination or fragment thereof. The reagent will comprise one or more molecules capable of specifically binding a nucleic acid sequence (DNA or RNA) encoding a gene, or the corresponding polypeptide.

The kit may comprise one or more nucleic acid reagents for the detection of mRNA encoding a gene (either sense or antisense). The one or more nucleic acid reagents may be used for hybridization and/or amplification of the mRNA encoding the gene. The kit may comprise one or more pairs of primers for amplifying the mRNA encoding the gene. The kit may further comprise samples of total mRNA derived from tissue of various physiological states, such as normal/non-diseased, and diseased (e.g., from a subject with ALS), for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting mRNA encoding a gene in a biological sample comprising oligonucleotide probes effective to bind with elevated affinity to mRNA encoding the gene in vitro or in situ and containers for each of these probes.

In a further embodiment, the invention encompasses a kit for use in determining the level of gene expression in a biological sample comprising one or more agents, such as, for example, one or more antibodies, specific for one or more polypeptides or fragments. In one particular embodiment, the kit will comprise one or more agents and one or more nucleic acid markers wherein the agents and nucleic acid markers are modified in a fashion appropriate for carrying out immuno-polymerase chain reaction assays.

One preferred embodiment of the invention is directed to a kit for determining the levels of gene expression in a mammalian biological sample, wherein said levels of marker expression is an indicator of the prognosis or diagnosis of ALS, said kit comprising: a) an antibody that specifically binds to a gene product or an antigen binding fragment thereof, b) a reagent useful for detecting the extent of interaction between said antibody and the marker; c) a reagent or solution useful for antigen retrieval; and c) positive and/or negative control samples. Said antibody may be directly linked to an indicator reagent, wherein said indicator reagent is selected from the group consisting of fluorescent, colorimetric, immunoperoxidase and isotopic reagents. Alternatively, the kit may further include a second indicator antibody linked to an indicator reagent, wherein said indicator reagent is selected from the group consisting of fluorescent, calorimetric, immunoperoxidase and isotopic reagents.

In one embodiment, the kit contains at least one primary antibody, at least one labeled secondary antibody, and at least one substrate (e.g., TMB). Alternatively, the kits can contain radiolabeled secondary antibody in place of the secondary antibody labeled with an enzyme. The kits may also contain disposable supplies for carrying out detection assays (e.g., microtiter plates, pipettes).

EXAMPLES

Example 1

FGGY Expression Correlates with ALS in Patients

Gastrocnemius muscle tissue samples and spinal cord and motor cortex samples were collected from living ALS patients (left Western Blot) and decease ALS patients (right Western Blot). The resulting muscle lysates were probed using an anti-FGGY antibody purchased from Santa Cruz Biotechnology® (FGGY J-5, sc130457) and the results are illustrated in FIG. 1. In particular, both living and deceased ALS patients showed significantly greater expression of FGGY protein in the muscle compared to the control samples. In addition, data from the spinal cord suggests that there is a general trend in increased FGGY protein expression, but more samples would be required to further validate this finding. The multiple bands detected by the anti-FGGY antibody in the Western Blots included above and herein may be due to changes in FGGY glycosylation or phosphorylation (mass spectrometry data not shown). Moreover, RT-PCR experiments were conducted using RNA samples from the same human subjects using FGGY primers (Forward) 5'-GGG GTG ATG TCT GTG GAA A-3' (SEQ ID NO. 7) and (Reverse) 3'-TCC CAG CAA ATC TCT CTC AAG-5' (SEQ ID NO. 8).

Example 2

FGGY Expression Correlates with Disease Severity

Samples from SOD1G93A mice (i.e., animals with a mutation in the superoxide dismutase 1 or SOD1 gene, which are a known model for ALS) (hereinafter "SOD1 mice") were collected and FGGY protein expression was assessed using an anti-FGGY antibody purchased from Santa Cruz Biotechnology® (FGGY J-5, sc130457) via Western Blot. In addition, GAPDH was measured as a loading control.

Figure 2:
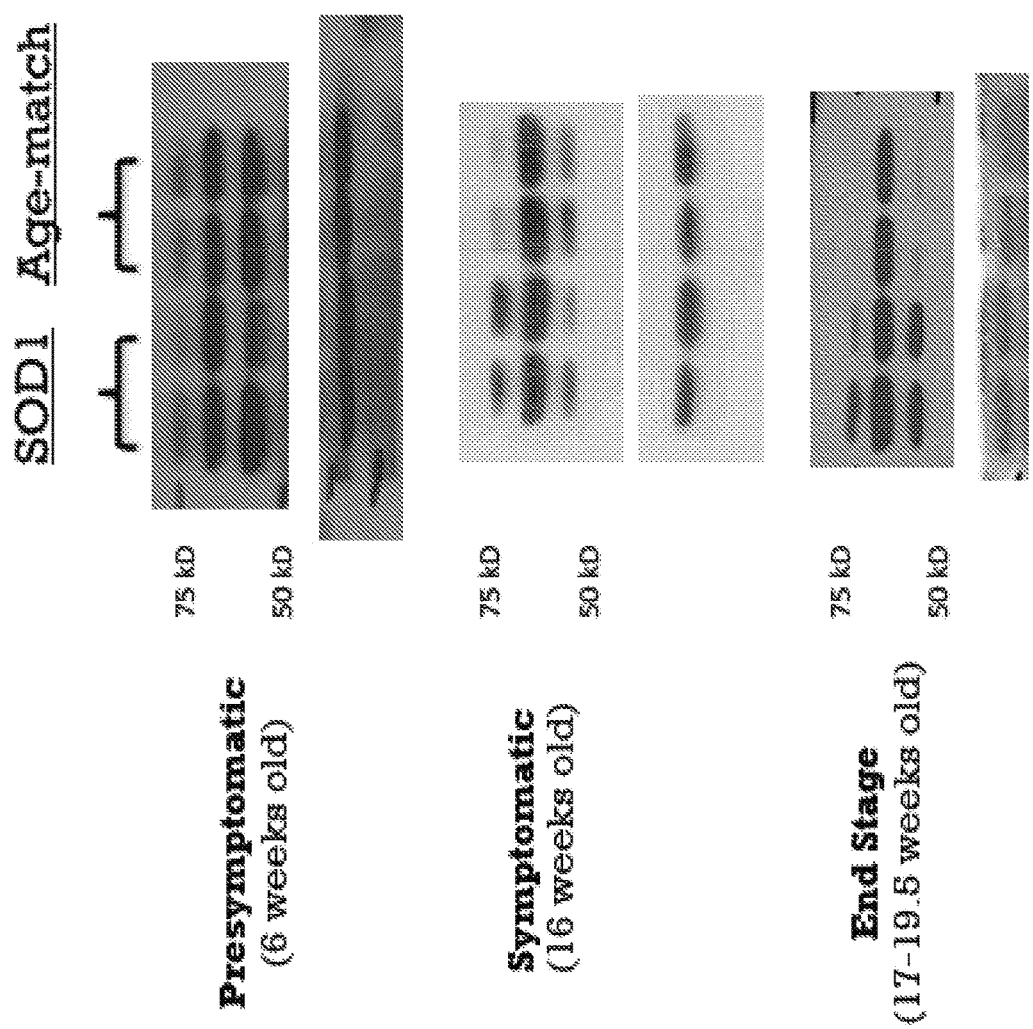
FIG. 2 is a set of Western Blots in which the FGGY protein expression levels in the muscles of SOD1G93A mice were examined. SOD1G93A ("SOD1") mice are animal models for ALS. In these experiments, SOD1 mice were age-matched to non-carriers of the SOD1 mutation and muscle samples were taken at different time points to assess FGGY protein expression levels, using GAPDH as a loading control. In the pre-symptomatic group (animals about 6 weeks of age), FGGY protein levels were generally similar between the SOD1 mice and the age-matched control animals. In the symptomatic group (animals about 16 weeks of age), FGGY protein levels in the SOD1 group are greater than FGGY protein levels in the age-matched control animals. Finally, in the end-stage group (animals about 17-19.5 weeks of age), FGGY protein expression is much greater in the SOD1 animals compared to the control animals.

Gastrocnemius muscle samples were taken from SOD1 and age-matched control mice at three different time points: (i) at six weeks of age (ALS-presymptomatic animals); (ii) at 16 weeks of age (ALS-symptomatic animals); and (iii) at 17 to 19.5 weeks of age (ALS-end stage animals). As illustrated in FIG. 2, FGGY protein expression was generally similar between the SOD1 mice and the age-matched control animals at the presymptomatic stage. Thereafter, in the symptomatic and end-stage groups, FGGY protein expression was determined to be significantly greater in the SOD1 mice compared to the age-matched control animals.

Example 3

FGGY Expression in the Spinal Cord

Figure 3:
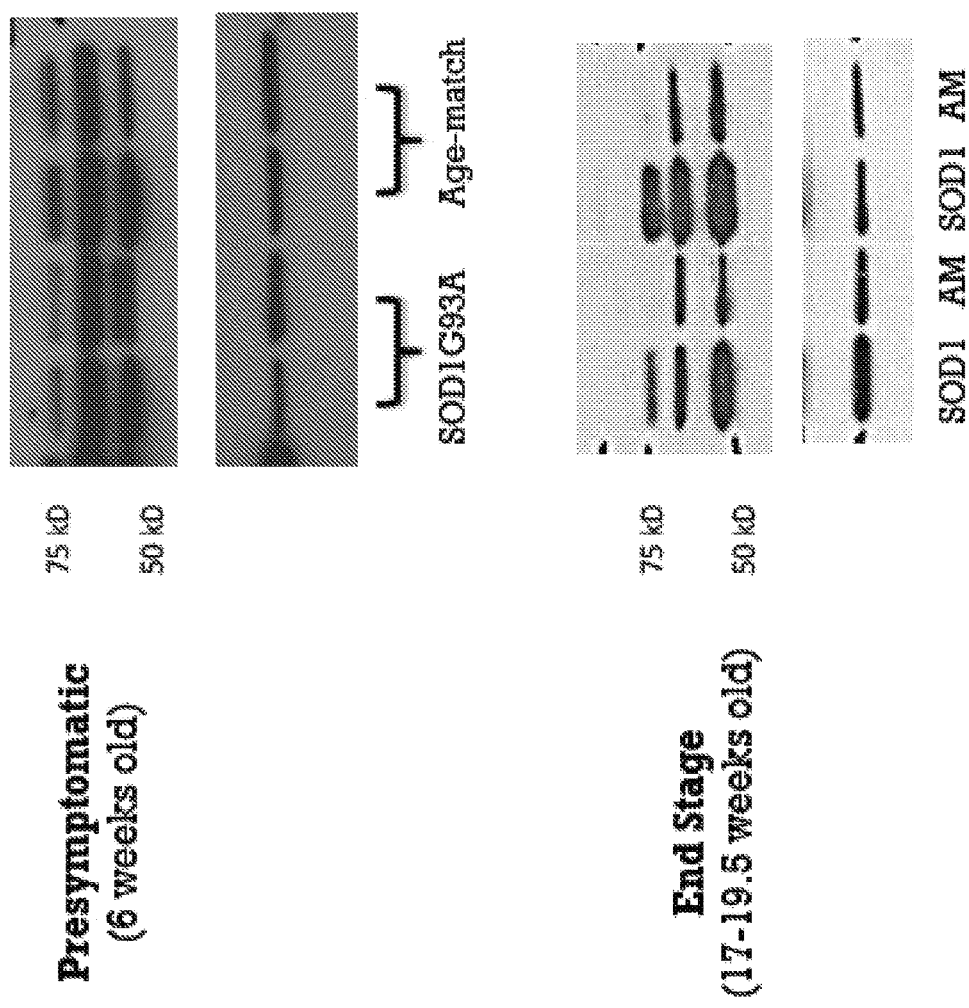
FIG. 3 is a set of Western Blots in which FGGY protein expression levels in the spinal cords of SOD1 mice were examined relative to age-matched control animals. In these experiments, SOD1 mice were age-matched to non-carriers of the SOD1 mutation and spinal cord samples were taken at different time points to assess FGGY protein expression levels, using GAPDH as a loading control. In the pre-symptomatic group (animals about 6 weeks of age), FGGY protein levels were generally similar between the SOD1 mice and the age-matched control animals. In the end-stage group (animals about 17-19.5 weeks of age), FGGY protein expression is much greater in the spinal cords of SOD1 animals compared to the control animals.

FGGY protein expression levels were detected in the spinal cords of SOD1 and age-matched control animals at two different time points: (i) at six weeks of age (ALS-presymptomatic animals); and (ii) at 17 to 19.5 weeks of age (ALS-end stage animals). As illustrated in FIG. 3, in the spinal cords, FGGY protein expression was generally similar between the SOD1 mice and the age-matched control animals at the presymptomatic stage. Thereafter, in the end-stage groups, a small change was noted in FGGY protein expression in the SOD1 mice compared to the age-matched control animals.

Example 4

Microscopic Validation of Murine FGGY Expression Data

Figure 4:
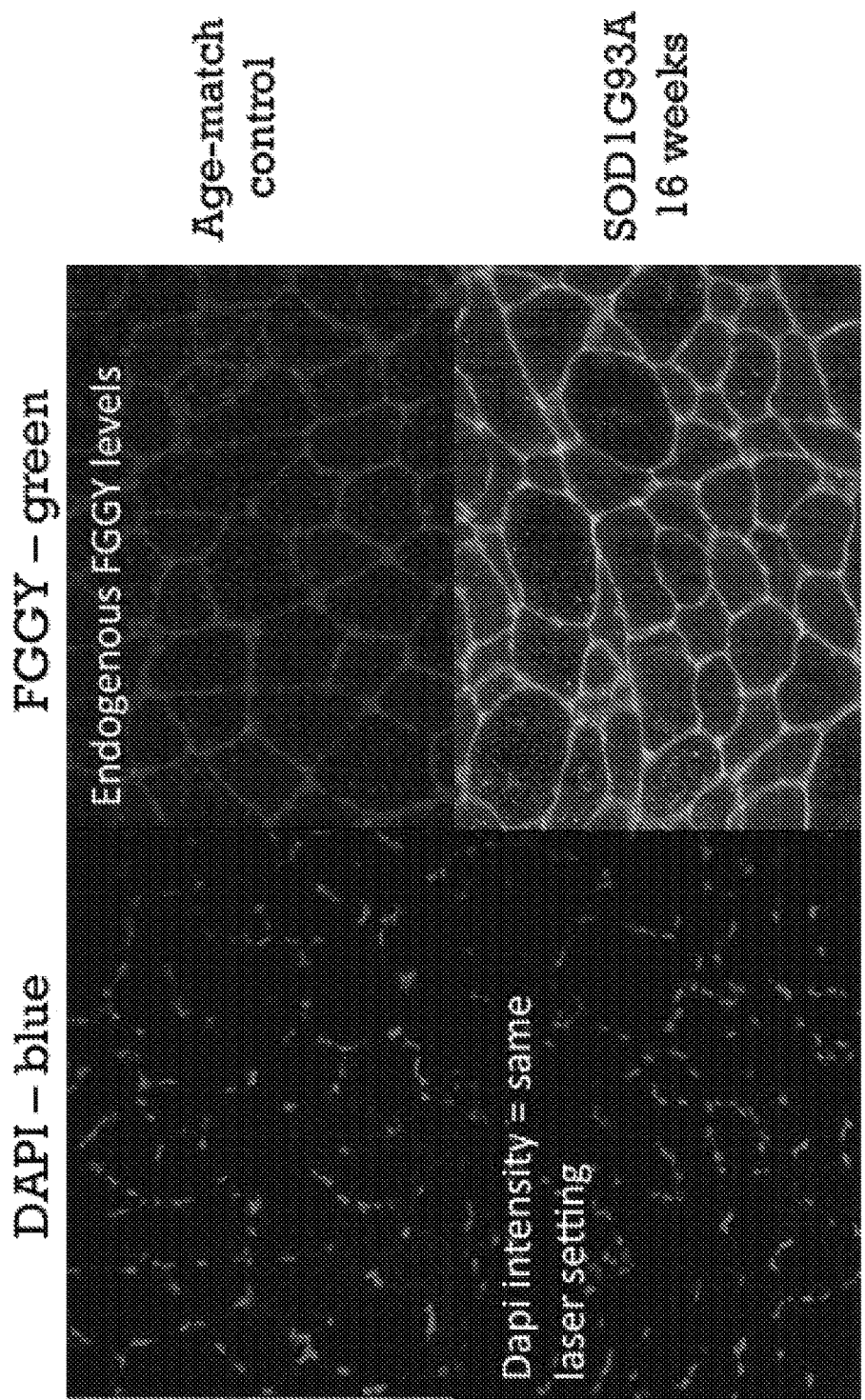
FIG. 4 is a set of immunofluorescence-stained microscopic images of FGGY protein expression. In these experiments, gastrocnemius muscles from SOD1 mice and age-matched control mice were stained for FGGY protein and stained using the nuclear stain 4',6-diamidino-2-phenylindole, DAPI. The intensity of the FGGY staining was much greater in the 16-week old SOD1 mice compared to the age-matched control animals.

Immunofluorescence microscopy was employed using gastrocnemius muscle samples from symptomatic SOD1 mice (i.e., about 16 weeks of age) and age-matched control animals. The samples were processed and stained using DAPI (i.e., to visualize the nucleus) and an anti-FGGY antibody purchased from Abcam® (ab77723). In addition, the tissue samples taken from the SOD1 and control mice were placed on the same microscope slide during processing so that the antibody concentrations, blocks, washes, and incubations would be identical for the two samples. As illustrated in the images of FIG. 4, FGGY protein levels are much great in the SOD1 mice compared to the age-matched control mice.

Example 5

Intracellular FGGY Localization

Figure 5:
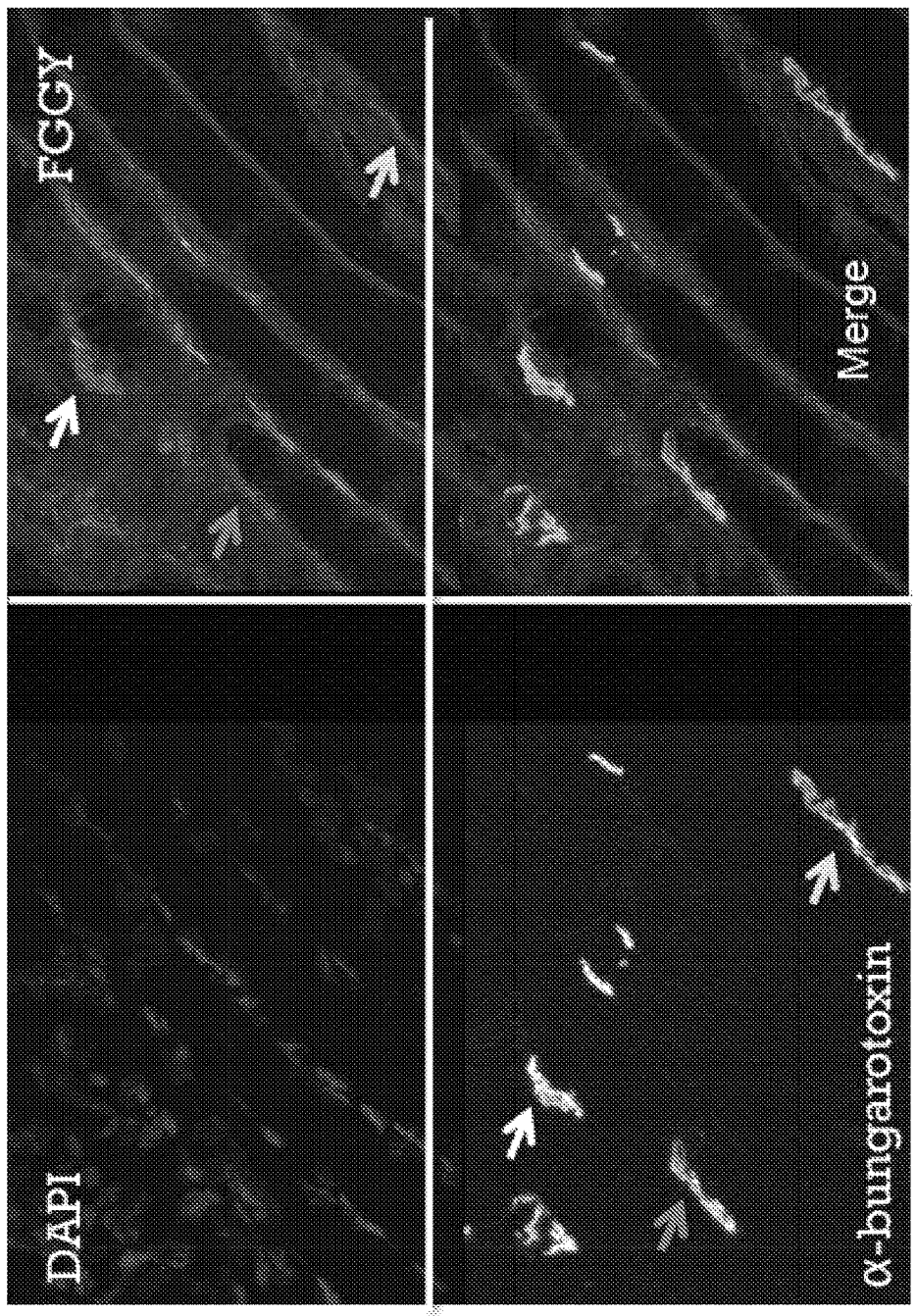
FIG. 5 is a set of immunofluorescence-stained microscopic images that show that FGGY protein expression co-localizes with the neuromuscular junction (NMJ). In these experiments, gastrocnemius muscles from SOD1 mice were stained for FGGY protein and stained using alpha-bungarotoxin, which stains acetylcholine receptors, thereby indicating the position of the NMJ. As reflected by the arrows in FIG. 5, the NMJ and FGGY staining co-localize in at least some of the muscle cells.

Next, experiments were conducted to assess where FGGY protein was localized within the muscle cells. In this experiment, a long section of gastrocnemius muscle was taken from symptomatic SOD1 mice. The neuromuscular junction (NMJ) is more readily visible in the long section sample of muscle. For these samples, the tissue was similarly stained with DAPI and an anti-FGGY antibody purchased from Abcam® (ab77723). In addition, the samples were stained with alpha-bungarotoxin, which stains acetylcholine receptors to provide visualization of the NMJ. As seen by the arrows in FIG. 5, FGGY expression at least partially co-localizes with the NMJ in the muscle cells.

Example 6

FGGY mRNA Expression Correlates with Protein Data for Disease Severity

Quantitative real-time PCR experiments were also conducted to assess changes in FGGY mRNA expression levels (SEQ ID NO. 1, SEQ ID NO. 3, and SEQ ID NO. 5). In these experiments, gastrocnemius muscle and lumbar spinal cord samples were taken from SOD1 and age-matched control mice at three different time points: (i) at six weeks of age (ALS-presymptomatic animals); (ii) at 16 weeks of age (ALS-symptomatic animals); and (iii) at 17 to 19.5 weeks of age (ALS-end stage animals). Thereafter, total RNA was isolated and cDNA was prepared using conventional methods known in the arts. Thereafter, quantitative real-time PCR was performed on the cDNA to assess expression of FGGY mRNA. The inventors used the following FGGY primers for these murine experiments (Forward) 5'-CAG TGG CAG CCT CAC TCA-3' (SEQ ID NO. 9) and (Reverse) 3'-CTC TCA CAT CTG CCC CAA TC-5' (SEQ ID NO. 10)

Figure 6:
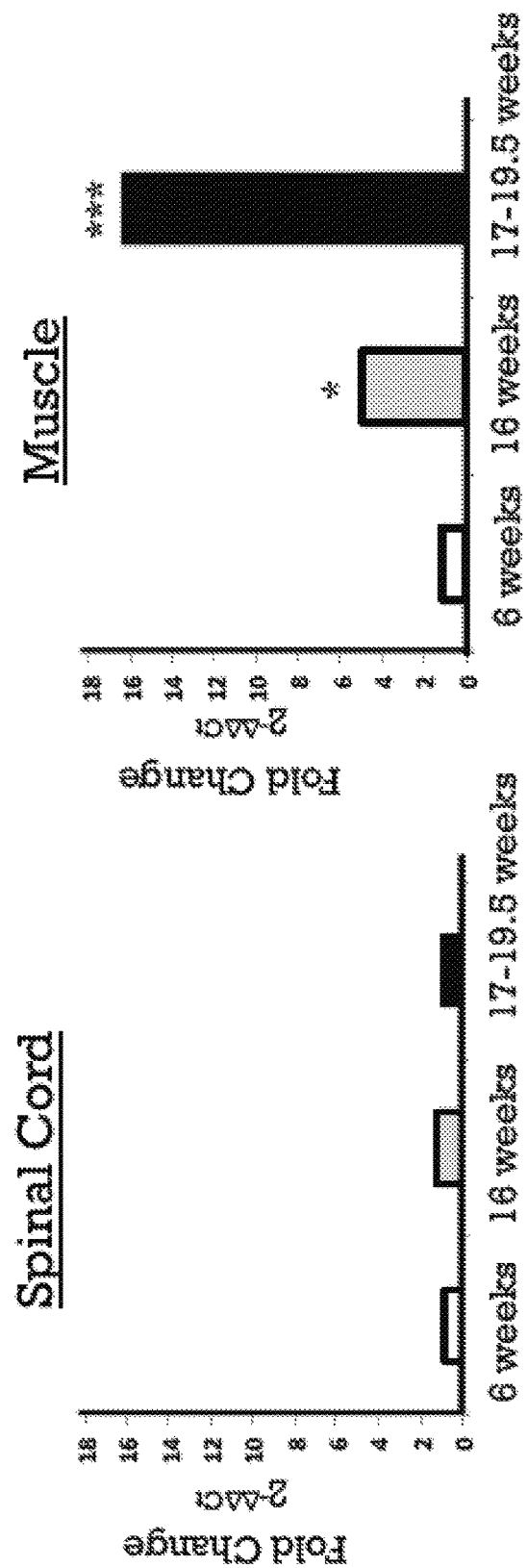
FIG. 6 is a set of bar graphs reflecting the change in FGGY mRNA expression in tissues of SOD1 mice. In these experiments, spinal cords and muscles from SOD1 mice and aged-matched control animals that had aged 6, 16, and 17-19.5 weeks were harvested and mRNA was isolated. The FGGY mRNA expression levels were assessed using quantitative RT-PCR. The expression of FGGY mRNA was significantly elevated compared to age-matched control animals in the muscle samples as disease severity progressed. No changes in FGGY mRNA expression were detected in the spinal cords of the SOD1 mice compared to the age-matched control animals.

As illustrated in FIG. 6, FGGY mRNA expression in muscle samples was generally similar between the SOD1 mice and the age-matched control animals at the presymptomatic stage for both muscle and spinal cord samples. Thereafter, in the muscle samples obtained from the symptomatic and end-stage groups, FGGY mRNA expression was determined to be significantly greater in the SOD1 mice compared to the age-matched control animals, with a nearly 16-fold increase seen in the end-stage SOD1 group. Conversely, no significant changes in FGGY mRNA expression were detected in the spinal cord samples for the symptomatic and end-stage groups.

Example 7

FGGY Expression in Non-SOD1 Animals

Changes in FGGY expression (i.e., protein or nucleotide expression) were assessed to determine whether expression is generally related to damage to the motor neurons or surrounding muscles or is specific to the SOD1-ALS model of disease. In these experiments, wild-type mice (C57BL/6) were used such that no animals were expected to exhibit symptoms of ALS. Surgical procedures were performed on different groups of animals. In a first set of animals that were used to assess FGGY mRNA expression in the spinal cord, surgery was performed on all of the mice to at least expose the sciatic nerve. In one-half of these animals, the sciatic nerve was crushed to provide a simulation of an acute injury. Seven days later, the animals were sacrificed and a portion of the spinal cord was harvested for quantitative RT-PCR experiments. In a second set of animals, the gastrocnemius muscle was crushed on one hindquarter of the mice, which includes crushing the sciatic nerve, and the second gastrocnemius muscle was left uncrushed, with no damage to the sciatic nerve. In this second set, seven days after injury, the animals were sacrificed and the gastrocnemius muscles (both crushed and uncrushed) were harvested for quantitative RT-PCR experiments. These experiments used the same primers discussed above, SEQ ID NO. 9 and SEQ ID NO. 10.

Figure 7:
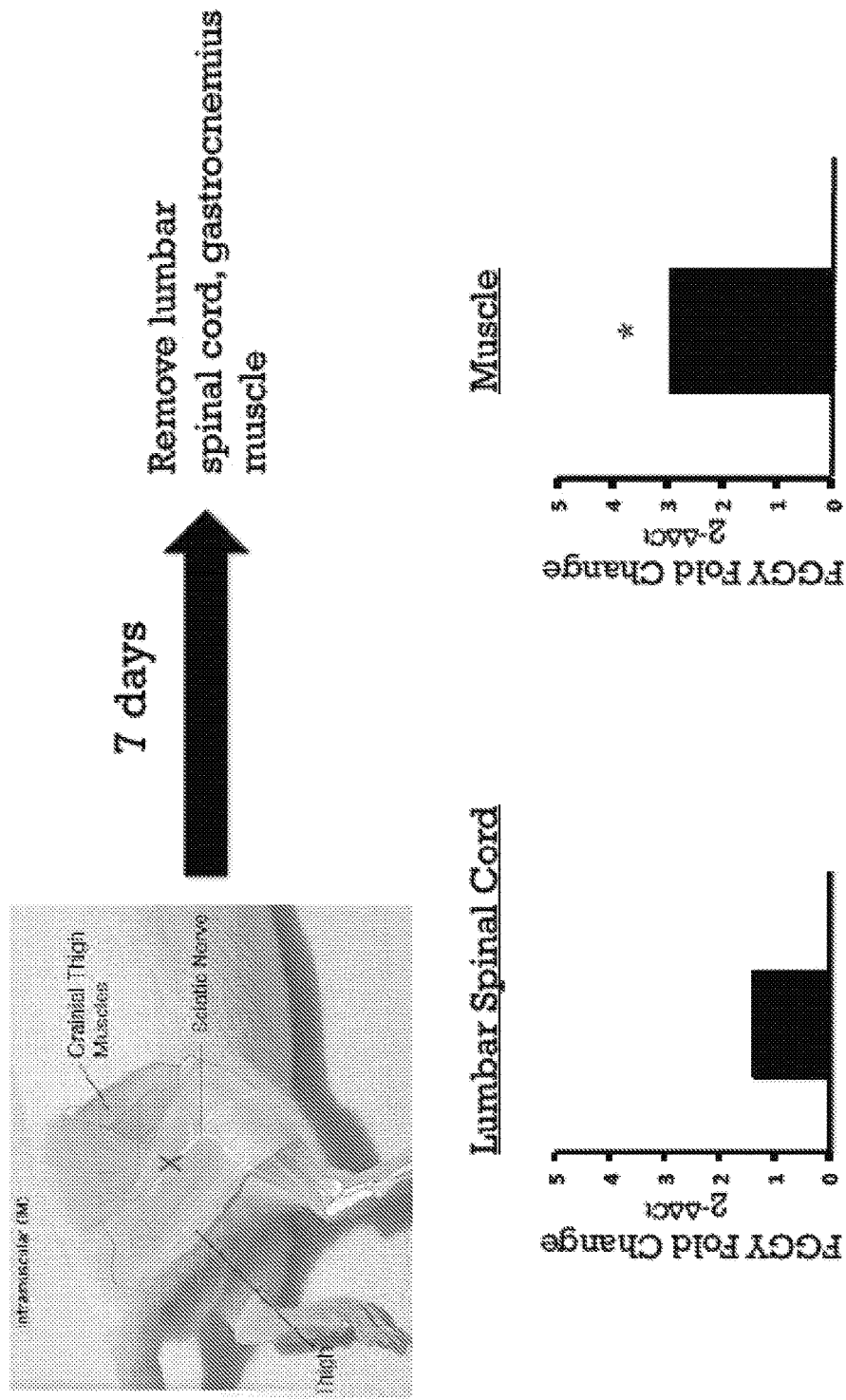
FIG. 7 details the general protocol and results for experiments conducted to assess changes in FGGY expression in response to muscle or nerve injury. In these experiments, wild-type C57BL/6 mice were used. In the experimental group, surgical procedures were performed to expose and crush one of each mouse's sciatic nerves. In the control group, the same procedures were performed, but the sciatic nerves were not crushed. Seven days after the procedures, the spinal cord and muscles were harvested and mRNA was isolated. The FGGY mRNA expression levels were assessed using quantitative RT-PCR. In comparison to the control animals, FGGY mRNA expression levels increased in the muscle in response to the acute nerve injury. No significant differences were detected in FGGY mRNA expression levels in the spinal cord.

As illustrated in FIG. 7, no significant changes in FGGY mRNA levels were noted in the spinal cord. In particular, seven days after undergoing a surgical procedure, animals that received acute sciatic nerve injuries, compared to those that only underwent a surgical procedure, did not exhibit increased FGGY mRNA expression levels in their spinal cords. Conversely, compared to uncrushed gastrocnemius muscles, the muscles that received a crushing injury and acute nerve injury exhibited a 3-fold increase in FGGY mRNA expression. This increase, while significant, was not of the same magnitude as the increases seen in the SOD1-ALS model mice.

Example 8

Putative FGGY-Binding Partners

In the experiments discussed above, changes in FGGY expression are generally correlated with ALS in both humans and non-human animals. In addition, changes in FGGY expression (e.g., increases in FGGY expression) are correlated with prognosis/disease severity. In addition to making these findings, the novel function of FGGY has been investigated, including making assessments of FGGY-binding partners (i.e., proteins or other molecules that bind FGGY during normal cell functioning). This information regarding FGGY-binding partners can be used to further elucidate the normal function of FGGY.

Multiple cell lines were grown and processed separately and under stringent immunoprecipitation conditions endogenous FGGY was captured using an immunoprecipitation assay that captured FGGY and whichever molecules were bound to FGGY. The resulting immunoprecipitated proteins were analyzed via mass spectrometry. The following methods were used in completing these experiments.

HeLa, H4 (human neuroglioma), and HEK293 ft cell lines were both cultured in Dulbecco's Modified Eagle Medium (Gibco-11995-073) containing 10% FBS, Penicillin (100 U/ml), Streptomycin (100 µg/ml), 4 mM l-glutamine, and 25 mM HEPES. Cells were passaged every 3 days based on 90% confluence. Passages were done using PBS (Gibco-10010-049) and 0.05% Trypsin-EDTA (1×) (Gibco-25300-062), Cells were maintained in a 37° C., 5% CO2 atmosphere.

Co-Immunoprecipitation (co-IP) was performed using HeLa and H4 Cell lines. Cells were seeded at $1.65 \times 10^6$ cells per 100 mm cell-culture dish. Cells were scraped and lysed in RIPA buffer (150 mM NaCl, 1.0% IGEPAL® CA-630, 0.5% sodium deoxycholate, 0.1% SDS, 50 mM Tris, pH 8.0-Sigma R0278) with 1× protease inhibitor and passed through a 21 gauge needle. Lysate was centrifuged at 4° C.

at 10,000×g for 15 min and the supernatant was taken for assay. The protein concentration of the lysate was determined via BCA; 750 µg of protein was used for each co-IP. Invitrogen's Dynabeads Protein G kit (100.07D) was used to carry out the co-immunoprecipitations. 1.5 mg of Dynabeads were blocked in 1% BSA in PBS for 1 hr at 4° C. with rotation, concurrently, 750 µg of cell lysate was precleared with an additional 1.5 mg of Dynabeads for 1 hr at 4° C. with rotation. The blocked beads were incubated with 2 µg of antibody (FGGY J5, FGGY ab77723, HnRNP C1/C2) or in PBS (for control) for 10 min at room temperature with rotation to form the Ab-bead complex. The Ab-bead complex and the bead alone control (in a separate tube) were incubated with the precleared lysate with rotation overnight at 4° C. to form bead-Ab-antigen complex (or bead-antigen complex). The bead complexes were washed with 500 µl of RIPA buffer (repeated 8 times) then resuspended in 20 µl Elution buffer and 10 µl of premixed Nupage LDS Sample Buffer+NuPage Sample Reducing Agent. This resuspension was heated for exactly 10 min at 70° C. The sample was loaded directly onto a NuPAGE 4-12% Bis-Tris Gel (NP0335BOX). The aforementioned western blotting procedure was then conducted and the blots were probed for each interaction (IP FGGY probe-FGGY, IP bead alone control probe-FGGY, IP HnRNPC probe-HnRNPC, IP bead alone control probe-HnRNPC, IP FGGY probe-HnRNPC, IP HnRNPC probe-FGGY).

The FGGY-immunoprecipitation products were eluted off the Dynabeads (see co-IP methods above) and run on a NuPAGE 4-12% Bis-Tris Gel. The gel was then stained with Bio-Safe Coomassie Stain (Bio-Rad 161-0786) for 1 hr with rotation. The gel was rinsed in water for 1 hr before each lane was cut into 5 segments. In-gel digestion was done and proteins were precipitated using a solution of cold acetone, 10% TCA, and 20 mM DTT incubated at −20° C. for 1 hr. After the initial centrifugation the pellet was washed an additional 2 times with cold acetone. The washed pellet was resuspened in 50 mM ammonium bicarbonate buffer pH 7.8, 50% trifluoroethanol (TFE), and 10 mM DTT and incubated at 60° C. for 1 hr. Proteins were alkylated using 30 mM iodoacetamide and incubated at room temperature for 30 min in the dark. The protein solution was diluted to reduce the TFE concentration to below 5% using ammonium bicarbonate buffer. For protein digestion, trypsin (Promega, Gold) was used at a protein:enzyme ratio of 50:1 and incubated overnight at 37° C. The digested protein solution was speed-vac to dryness and reconstituted using 0.1% formic acid.

LC-MS/MS analysis was performed using a Thermo LTQ Orbitrap Velos operating in positive mode. A Thermo nanospray head coupled with a coated PicoTip fused silica spray tip (360 µm OD, 20 µm ID, 10 µm diameter emitter orifice, New Objective, Woburn, Mass., USA) was used as the ionization source. Samples were analyzed using an ion spray voltage and heated capillary temperature of 1.9 kV and 220° C., respectively. Data dependent acquisition was used in the mass spectrometry analysis, in which a high resolution (60,000) MS survey scan (m/z 300-2000) with orbitrap (AGC: 1,000,000) was followed by 15 data dependent product ion scans of the most intense precursor ions in the LTQ (AGC: 10,000) with an isolation window of 2 Da, a collision energy of 35, and activation time of 30 ms. Dynamic exclusion was used with repeat counts, repeat duration, and exclusion duration of 1, 30 s, and 60 s, respectively. Peptides were separated by nanoflow liquid chromatography using a Waters nanoAcquity LC system. Digested peptides were analyzed by injecting 2 µg of the digest onto a trap column (Symmetry C18 5 µm 180 µm×20 mm, Waters Co., Milford, Mass., USA) for preconcentration at a flow rate of 5 uL/min for 3 min using 99% solvent A and 1% solvent B (solvent A: H2O with 0.1% v/v formic acid, solvent B: acetonitrile with 0.1% v/v formic acid). Peptides were then separated with a BEH130 C18 column (1.7 µm, 100 µm×100 mm, Waters Co., Milford, Mass., USA) using an analytical gradient from 1% to 60% mobile solvent B over 90 min.

For MS/MS data, peptides were initially identified by searching against the human protein database from the National Center for Biotechnology Information (NCBI) using the SEQUEST algorithm (ThermoElectron, San Jose, Calif.). Further processing to verify peptide identifications assigned by SEQUEST and to validate protein identifications derived from MS/MS data (min protein: 95.0%, min # peptides: 3, min peptide: 95%) was performed using Scaffold 3 (Proteome Software Inc., Portland Oreg.) with the X!Tandem database searching program.

The results from this immunoprecipitation assay (not shown) indicated that a significant number of binding partners for FGGY are associated with RNA metabolism. The results included several heterogeneous nuclear ribonuclearproteins (HnRNP), including HnRNP A, C, R, K, and U. To date, there have been no reported associations between HnRNP and ALS.

Figure 8:
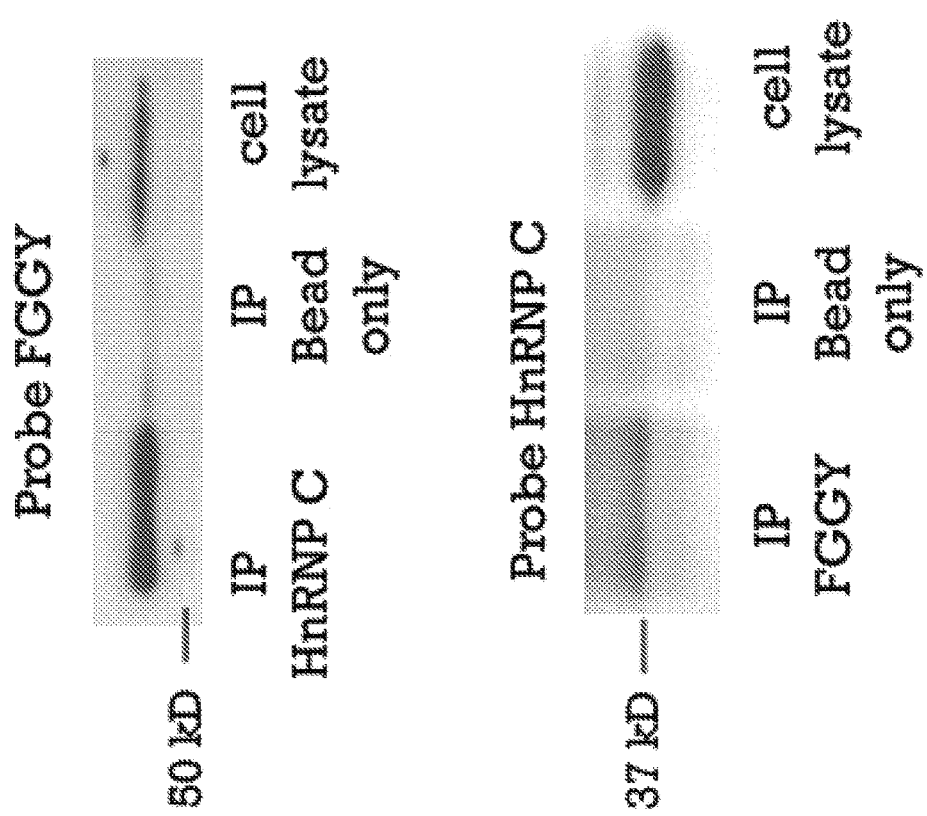
FIG. 8 is a set of Western Blots of an immunoprecipitation assay showing the binding of FGGY to heterogenous nuclear ribonucleoprotein C (HnRNP C). In these experiments, proteins in lysates from immortalized cells were co-immunoprecipitated under stringent conditions using either anti-FGGY immunoprecipitation beads or anti-HnRNP C immunoprecipitation beads. The resulting immunoprecipitation mixture was probed with either anti-FGGY antibodies or anti-HnRNP C antibodies. As illustrated in the Western Blots, FGGY co-immunoprecipitates with HnRNP C meaning that the two proteins bind together.

In order to validate the findings related to HnRNP, co-immunoprecipitations were performed on FGGY and HnRNP C. Specifically, both HeLa and HEK293 cells were grown, lysed, and immunoprecipitated using anti-HnRNP C immunoprecipitation beads or using anti-FGGY immunoprecipitation beads. In addition to the immunoprecipitates, the immunoprecipitate beads alone and a total cell lysate were also gathered as controls. As shown in FIG. 8, by using anti-HnRNP C beads and then probing with an anti-FGGY antibody (upper Western Blot), FGGY protein was detected. Similarly, by using an anti-FGGY immunoprecipitation bead and then probing with an anti-HnRNP C antibody, HnRNP C protein was detected.

Figure 9A:
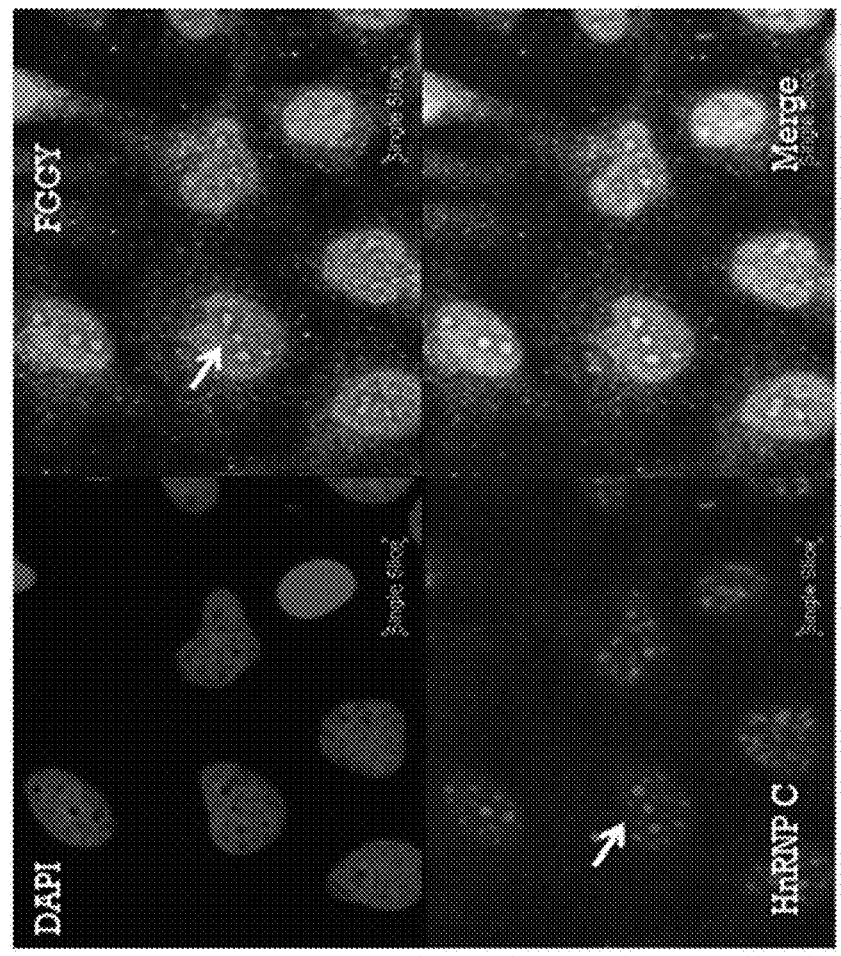
FIGS. 9A-9C show a set of immunofluorescence-stained microscopic images that illustrate the co-localization of FGGY with HnRNP C, Fibrillarin, and SMN1.
Figure 9C:
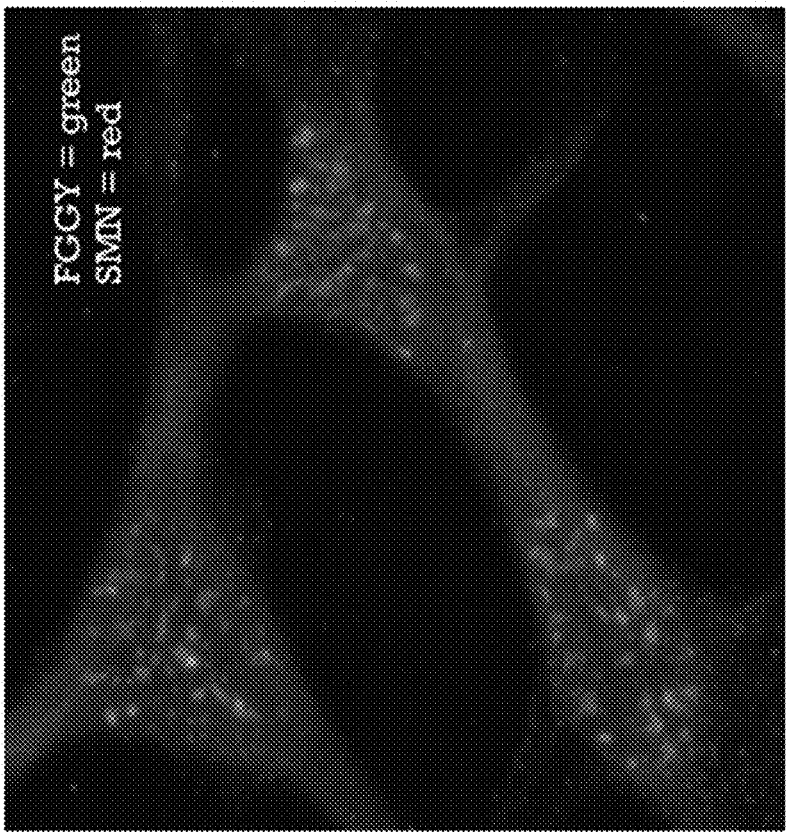
Figure 9B:
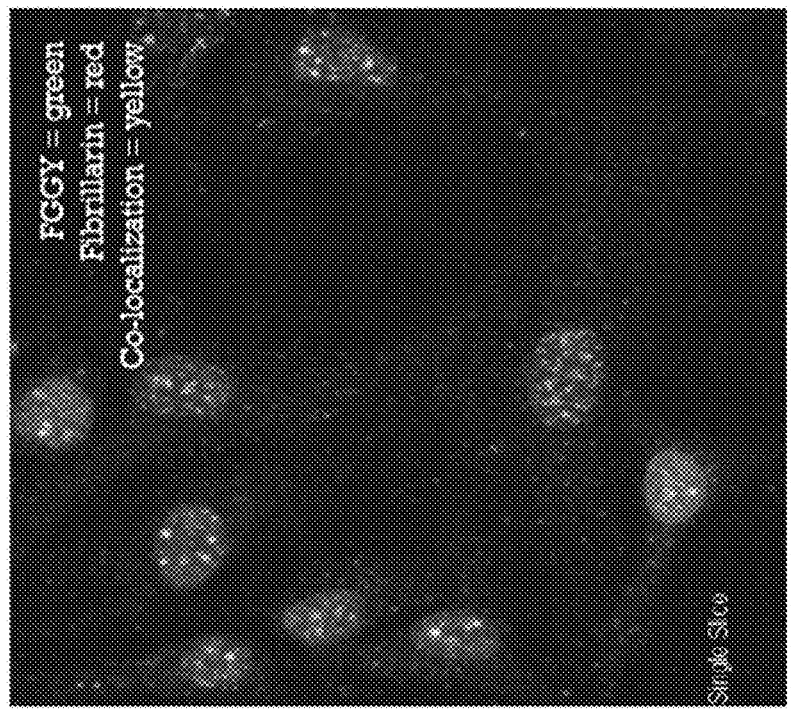

Finally, experiments were conducted to assess FGGY co-localization with different key cellular proteins. Referring to FIGS. 9A-9C, cells were grown to sufficient levels and then stained using DAPI, anti-FGGY antibodies, and antibodies to one of the following HnRNP C, Fibrillarin, and SMN1 to assess co-localization with FGGY via merged images. In panel A in FIG. 9A, HEK293 cells were used for the experiment in which FGGY showed a high degree of co-localization of staining with HnRNP C in the nucleus (i.e., the Merge frame). Moreover, based on the merged image, it appears that the FGGY-HnRNP C co-localization occurs in the nucleolus, which is the site of ribosomal RNA transcription and assembly. In order to further investigate the co-localization, HEK293 cells were stained with FGGY and Fibrillarin, a nucleolar protein. As show in panel B in FIG. 9B, FGGY also co-localizes with Fibrillarin, which means that FGGY protein can be found in the nucleolus. Finally, the co-localization of FGGY was assessed with Survival of Motor Neuron 1 (SMN1) in HeLa cells. SMN1 is another protein that has been previously shown to be present within the nucleus. As shown in panel C in FIG. 9C, FGGY and SMN1 are closely associated in the nucleus of HeLa cells.

What is claimed is:

1. A method of determining whether a subject is likely to have amyotrophic lateral sclerosis, the method comprising the steps of:
receiving a muscle sample from the subject;
adding a reagent capable of binding to a marker selected from the group consisting of SEQ ID NO: 2, SEQ ID NO: 4, and SEQ ID NO: 6 to a mixture comprising the muscle sample;
subjecting the mixture to conditions that allow detection of binding of the reagent to the marker;
assessing an expression level of the marker in the muscle sample and a control sample, wherein assessing the expression level comprises determining a level of binding of the reagent to the marker in the muscle sample and determining a level of binding to the marker in the control sample; and
determining that the subject has amyotrophic lateral sclerosis when the expression level of the marker in the muscle sample is greater than the expression level of the marker in the control sample.

2. The method of claim 1, wherein the subject is a mammal.

3. The method of claim 2, wherein the subject is a human.

4. The method of claim 1, wherein the muscle sample comprises a sample of a gastrocnemius muscle from the subject.

5. The method of claim 1, wherein the reagent is an antibody.

6. The method of claim 1, wherein the reagent is capable of binding to a first marker consisting of SEQ ID NO: 2, a second marker consisting of SEQ ID NO: 4, and a third marker consisting of SEQ ID NO: 6.

7. A method of characterizing disease severity in a subject with amyotrophic lateral sclerosis, the method comprising the steps of:
receiving a tissue sample of muscle from the subject;
adding a reagent capable of binding to a marker selected from the group consisting of SEQ ID NO: 2, SEQ ID NO: 4, and SEQ ID NO: 6 to a mixture comprising the tissue sample;
subjecting the mixture to conditions that allow detection of binding of the reagent to the marker;
assessing an expression level of the marker in the tissue sample and a control sample, wherein assessing the expression level comprises determining a level of binding of the reagent to the marker in the tissue sample and determining a level of binding to the marker in the control sample; and
characterizing the amyotrophic lateral sclerosis as severe in the subject when the expression level of the marker in the tissue sample is greater than the expression level of the marker in the control sample.

8. The method of claim 7, wherein the muscle sample comprises gastrocnemius muscle.

9. The method of claim 7, wherein the reagent comprises an antibody.

10. The method of claim 7, wherein the control sample is derived from a subject that does not have amyotrophic lateral sclerosis.

11. The method of claim 7, wherein the reagent is capable of binding to a first marker consisting of SEQ ID NO: 2, a second marker consisting of SEQ ID NO: 4, and a third marker consisting of SEQ ID NO: 6.

12. A method of determining whether a subject is likely to have amyotrophic lateral sclerosis, the method comprising the steps of:
receiving a muscle sample from the subject;
adding a first antibody that is capable of binding to FGGY protein to a mixture comprising the muscle sample;
subjecting the mixture to conditions that allow detection of binding of the first antibody to the FGGY protein;
assessing an expression level of the FGGY protein in the muscle sample and a control muscle sample, wherein assessing the expression level comprises determining a level of binding of the first antibody to the FGGY protein in the muscle sample and determining a level of binding of the first antibody to the FGGY protein in the control muscle sample; and
determining that the subject is likely to have amyotrophic lateral sclerosis when the expression level the FGGY protein in the muscle sample is greater than the binding of the first antibody to the control muscle sample.

13. The method of claim 12, wherein the subject is a human.

14. The method of claim 12 and further comprising adding a second antibody to the mixture, wherein the second antibody is capable of binding to the first antibody.

15. The method of claim 12, wherein the method comprises a technique selected from the group consisting of flow cytometry, immunohistochemistry, enzyme-linked immunosorbent assay (ELISA), Western Blot, and immunoaffinity chromatography.

16. The method of claim 12, wherein the muscle sample comprises a gastrocnemius muscle sample.

* * * * *

SEQUENCE LISTING

<160> NUMBER OF SEQ ID NOS: 6

<210> SEQ ID NO 1
<211> LENGTH: 2102
<212> TYPE: DNA
<213> ORGANISM: Homo sapiens

<400> SEQUENCE: 1

| | | | | | |
|---|---|---|---|---|---|
| gctggtgcgc | aggctcttag | cgcgcacgcc | cagaaagagg | cttctccaac | ccggcccggc | 60 |
| ccttccttcc | cctttcccgc | agtcgttgcc | tcctcctccc | ctgcctcctc | ctcccctttcc | 120 |
| tcctcctggc | cgcttagtct | cacacccgcc | gggccgttgt | tcccgagacg | ttgttgagtc | 180 |
| ccctgtgtcc | tcttctgggt | ggaggaactg | caatgtctgg | tggagaacag | aaaccagaga | 240 |
| ggtactatgt | gggtgtggac | gttggaacag | gcagtgtccg | tgcagctctg | gtggaccaga | 300 |
| gtggggtcct | gttggctttt | gcagaccagc | caattaagaa | ttgggagccc | cagttcaacc | 360 |
| accatgagca | gtcctccgag | gacatctggg | ctgcgtgctg | tgttgtcaca | aagaaagttg | 420 |
| tacaagggat | tgatttaaac | caaattcgag | gacttgggtt | tgatgccacg | tgttctctgg | 480 |
| ttgttttgga | taagcagttt | cacccattac | cagtcaacca | ggaagggdat | tcccatcgaa | 540 |
| acgtcatcat | gtggctggac | catcgagcag | tcagtcaagt | taacaggatc | aatgagacca | 600 |
| agcacagtgt | cctccagtac | gtcggggggg | tgatgtctgt | ggaaatgcag | gccccgaaac | 660 |
| ttctgtggct | gaaagagaac | ttgagagaga | tttgctggga | taaggcggga | catttctttg | 720 |
| atctcccgga | cttcttatcg | tggaaggcaa | caggtgtcac | agcacggtct | ctctgctccc | 780 |
| tggtgtgtaa | gtggacatat | tcagcagaga | aaggctggga | cgacagtttc | tggaaaatga | 840 |
| ttggttttgga | agactttgtt | gcagataatt | acagcaaaat | aggaaaccaa | gtgctacctc | 900 |
| ctggagcttc | tcttggaaat | gggctcacac | cagaggcagc | aagagacctt | ggccttctcc | 960 |
| ctgggattgc | ggtcgcagct | tcactcattg | atgcccatgc | aggaggacta | ggagtgattg | 1020 |
| gggcagatgt | gagagggcac | ggcctcatct | gtgaggggca | gccagtgacg | tcacggctgg | 1080 |
| ctgtcatctg | tggaacgtct | tcttgtcaca | tgggatcag | caaagacccg | attttttgtac | 1140 |
| caggcgtctg | ggggccttat | ttctcagcca | tggtacctgg | gttctggctg | aatgaaggtg | 1200 |
| gtcagagcgt | tactgaaaaa | ttgatagacc | acatggtaca | aggccatgct | gcttttccag | 1260 |
| aactacaagt | aaaggccaca | gccagatgcc | agagtatata | tgcatatttg | aacagtcacc | 1320 |
| tggatctgat | taagaaggct | cagcctgtgg | gttttccttac | tgttgattta | catgtttggc | 1380 |
| cagatttcca | tggcaaccgg | tctcccttag | cagatctgac | actaaagggc | atgagaacca | 1440 |
| ctggatatct | gtatattccg | gctttggcag | cgttgcactc | tcccagttct | ctactctccc | 1500 |
| ctcaggtcac | cggattgaaa | ctgtctcagg | accttgatga | tcttgccatt | ctctacctgg | 1560 |
| ccacagttca | agccattgct | ttggggactc | gcttcattat | agaagccatg | gaggcagcag | 1620 |
| ggcactcaat | cagtactctt | ttcctatgtg | gaggcctcag | caagaatccc | cttttttgtgc | 1680 |
| aaatgcatgc | ggacattact | ggcatgcctg | tggtcctgtc | gcaagaggtg | gagtccgttc | 1740 |
| ttgtgggtgc | tgctgttctg | ggtgcctgtg | cctcagggga | tttcgcttct | gtacaggaag | 1800 |
| caatggcaaa | aatgagcaaa | gttgggaaag | ttgtgttccc | gagactacag | gataaaaaat | 1860 |
| actatgataa | gaaataccaa | gtattcctga | agctggttga | acaccagaag | gagtatttgg | 1920 |
| cgatcatgaa | tgatgactga | acagggcttg | caggtgctga | tgccagaagc | ttctgtgcca | 1980 |
| ttgcattaaa | gacttgtcat | ttgatccatg | ttcaagaccc | ttgaggtatt | gtttcatcat | 2040 |
| ttctgtattg | tctttcaata | aagaaaacaa | acatgtgcaa | ccagaaaaaa | aaaaaaaaaa | 2100 | aa                                                                   2102

<210> SEQ ID NO 2
<211> LENGTH: 575
<212> TYPE: PRT
<213> ORGANISM: Homo sapiens

<400> SEQUENCE: 2

Met Ser Gly Gly Glu Gln Lys Pro Glu Arg Tyr Tyr Val Gly Val Asp
1               5                   10                  15

Val Gly Thr Gly Ser Val Arg Ala Ala Leu Val Asp Gln Ser Gly Val
            20                  25                  30

Leu Leu Ala Phe Ala Asp Gln Pro Ile Lys Asn Trp Glu Pro Gln Phe
        35                  40                  45

Asn His His Glu Gln Ser Ser Glu Asp Ile Trp Ala Ala Cys Cys Val
    50                  55                  60

Val Thr Lys Lys Val Val Gln Gly Ile Asp Leu Asn Gln Ile Arg Gly
65                  70                  75                  80

Leu Gly Phe Asp Ala Thr Cys Ser Leu Val Val Leu Asp Lys Gln Phe
                85                  90                  95

His Pro Leu Pro Val Asn Gln Glu Gly Asp Ser His Arg Asn Val Ile
            100                 105                 110

Met Trp Leu Asp His Arg Ala Val Ser Gln Val Asn Arg Ile Asn Glu
        115                 120                 125

Thr Lys His Ser Val Leu Gln Tyr Val Gly Gly Val Met Ser Val Glu
    130                 135                 140

Met Gln Ala Pro Lys Leu Leu Trp Leu Lys Glu Asn Leu Arg Glu Ile
145                 150                 155                 160

Cys Trp Asp Lys Ala Gly His Phe Phe Asp Leu Pro Asp Phe Leu Ser
                165                 170                 175

Trp Lys Ala Thr Gly Val Thr Ala Arg Ser Leu Cys Ser Leu Val Cys
            180                 185                 190

Lys Trp Thr Tyr Ser Ala Glu Lys Gly Trp Asp Asp Ser Phe Trp Lys
        195                 200                 205

Met Ile Gly Leu Glu Asp Phe Val Ala Asp Asn Tyr Ser Lys Ile Gly
    210                 215                 220

Asn Gln Val Leu Pro Pro Gly Ala Ser Leu Gly Asn Gly Leu Thr Pro
225                 230                 235                 240

Glu Ala Ala Arg Asp Leu Gly Leu Leu Pro Gly Ile Ala Val Ala Ala
                245                 250                 255

Ser Leu Ile Asp Ala His Ala Gly Gly Leu Gly Val Ile Gly Ala Asp
            260                 265                 270

Val Arg Gly His Gly Leu Ile Cys Glu Gly Gln Pro Val Thr Ser Arg
        275                 280                 285

Leu Ala Val Ile Cys Gly Thr Ser Ser Cys His Met Gly Ile Ser Lys
    290                 295                 300

Asp Pro Ile Phe Val Pro Gly Val Trp Gly Pro Tyr Phe Ser Ala Met
305                 310                 315                 320

Val Pro Gly Phe Trp Leu Asn Glu Gly Gly Gln Ser Val Thr Gly Lys
                325                 330                 335

Leu Ile Asp His Met Val Gln Gly His Ala Ala Phe Pro Glu Leu Gln
            340                 345                 350

Val Lys Ala Thr Ala Arg Cys Gln Ser Ile Tyr Ala Tyr Leu Asn Ser
        355                 360                 365

```
His Leu Asp Leu Ile Lys Lys Ala Gln Pro Val Gly Phe Leu Thr Val
    370                 375                 380

Asp Leu His Val Trp Pro Asp Phe His Gly Asn Arg Ser Pro Leu Ala
385                 390                 395                 400

Asp Leu Thr Leu Lys Gly Met Arg Thr Thr Gly Tyr Leu Tyr Ile Pro
                405                 410                 415

Ala Leu Ala Ala Leu His Ser Pro Ser Ser Leu Leu Ser Pro Gln Val
            420                 425                 430

Thr Gly Leu Lys Leu Ser Gln Asp Leu Asp Asp Leu Ala Ile Leu Tyr
        435                 440                 445

Leu Ala Thr Val Gln Ala Ile Ala Leu Gly Thr Arg Phe Ile Ile Glu
    450                 455                 460

Ala Met Glu Ala Ala Gly His Ser Ile Ser Thr Leu Phe Leu Cys Gly
465                 470                 475                 480

Gly Leu Ser Lys Asn Pro Leu Phe Val Gln Met His Ala Asp Ile Thr
                485                 490                 495

Gly Met Pro Val Val Leu Ser Gln Glu Val Glu Ser Val Leu Val Gly
            500                 505                 510

Ala Ala Val Leu Gly Ala Cys Ala Ser Gly Asp Phe Ala Ser Val Gln
        515                 520                 525

Glu Ala Met Ala Lys Met Ser Lys Val Gly Lys Val Val Phe Pro Arg
    530                 535                 540

Leu Gln Asp Lys Lys Tyr Tyr Asp Lys Lys Tyr Gln Val Phe Leu Lys
545                 550                 555                 560

Leu Val Glu His Gln Lys Glu Tyr Leu Ala Ile Met Asn Asp Asp
                565                 570                 575

<210> SEQ ID NO 3
<211> LENGTH: 2030
<212> TYPE: DNA
<213> ORGANISM: Homo sapiens

<400> SEQUENCE: 3
gctggtgcgc aggctcttag cgcgcacgcc cagaaagagg cttctccaac ccggcccggc      60
ccttccttcc cctttcccgc agtcgttgcc tcctcctccc ctgcctcctc ctccccttcc     120
tcctcctggc cgcttagtct cacacccgcc gggccgttgt tcccgagacg ttgttgagtc     180
ccctgtgtcc tcttctgggt ggaggaactg caatgtctgg tggagaacag aaaccagaga     240
ggtactatgt gggtgtggac gttggaacag gcagtgtccg tgcagctctg gtggaccaga     300
gtggggtcct gttggctttt gcagaccagc caattaagaa ttgggagccc cagttcaacc     360
accatgagca gtcctccgag gacatctggg ctgcgtgctg tgttgtcaca agaaagttg      420 tacagggat tgatttaaac caaattcgag gacttgggtt tgatgccacg tgttctctgg      480 ttgtttgga taagcagttt cacccattac cagtcaacca ggaagggat tcccatcgaa      540 acgtcatcat gtggctggac catcgagcag tcagtcaagt taacaggatc aatgagacca     600
agcacagtgt cctccagtac gtcgggggg tgatgtctgt ggaaatgcag gccccgaaac     660
ttctgtggct gaaagagaac ttgagagaga tttgctggga taaggcggga catttctttg     720
atctcccgga cttcttatcg tggaaggcaa caggtgtcac agcacggtct ctctgctccc     780
tggtgtgtaa gtggacatat tcagcagaga aaggctggga cgacagtttc tggaaaatga     840
ttggtttgga agactttgtt gcagataatt acagcaaaat aggaaaccaa gtgctacctc     900
ctggagcttc tcttggaaat gggctcacac cagaggcagc aagagacctt ggccttctcc     960
```

```
ctgggattgc ggtcgcagct tcactcattg atgcccatgc aggaggacta ggagtgattg    1020
gggcagatgt gagagggcac ggcctcatct gtgaggggca gccagtgacg tcacggctgg    1080
ctgtcatctg tggaacgtct tcttgtcaca tggggatcag caaagacccg attttttgtac   1140
caggcgtctg ggggccttat ttctcagcca tggtacctgg gttctggctg aatgaaggtg    1200
gtcagagcgt tactggaaaa ttgatagacc acatggtaca aggccatgct gcttttccag    1260
aactacaagt aaaggccaca gccagatgcc agagtatata tgcatatttg aacagtcacc    1320
tggatctgat taagaaggct cagcctgtgg gtttccttac tgttgattta catgtttggc    1380
cagatttcca tggcaaccgg tctcccttag cagatctgac actaaagggc atggtcaccg    1440
gattgaaact gtctcaggac cttgatgatc ttgccattct ctacctggcc acagttcaag    1500
ccattgcttt ggggactcgc ttcattatag aagccatgga ggcagcaggg cactcaatca    1560
gtactctttt cctatgtgga ggcctcagca agaatcccct ttttgtgcaa atgcatgcgg    1620
acattactgg catgcctgtg gtcctgtcgc aagaggtgga gtccgttctt gtgggtgctg    1680
ctgttctggg tgcctgtgcc tcaggggatt tcgcttctgt acaggaagca atggcaaaaa    1740
tgagcaaagt tgggaaagtt gtgttcccga gactacagga taaaaaatac tatgataaga    1800
aataccaagt attcctgaag ctggttgaac accagaagga gtatttggcg atcatgaatg    1860
atgactgaac agggcttgca ggtgctgatg ccagaagctt ctgtgccatt gcattaaaga    1920
cttgtcattt gatccatgtt caagacccttt gaggtattgt ttcatcattt ctgtattgtc    1980
tttcaataaa gaaacaaac atgtgcaacc agaaaaaaaa aaaaaaaaa                  2030
```

<210> SEQ ID NO 4
<211> LENGTH: 551
<212> TYPE: PRT
<213> ORGANISM: Homo sapiens
<400> SEQUENCE: 4

```
Met Ser Gly Gly Glu Gln Lys Pro Glu Arg Tyr Tyr Val Gly Val Asp
1               5                   10                  15

Val Gly Thr Gly Ser Val Arg Ala Ala Leu Val Asp Gln Ser Gly Val
            20                  25                  30

Leu Leu Ala Phe Ala Asp Gln Pro Ile Lys Asn Trp Glu Pro Gln Phe
        35                  40                  45

Asn His His Glu Gln Ser Ser Glu Asp Ile Trp Ala Ala Cys Cys Val
    50                  55                  60

Val Thr Lys Lys Val Val Gln Gly Ile Asp Leu Asn Gln Ile Arg Gly
65                  70                  75                  80

Leu Gly Phe Asp Ala Thr Cys Ser Leu Val Val Leu Asp Lys Gln Phe
                85                  90                  95

His Pro Leu Pro Val Asn Gln Glu Gly Asp Ser His Arg Asn Val Ile
            100                 105                 110

Met Trp Leu Asp His Arg Ala Val Ser Gln Val Asn Arg Ile Asn Glu
        115                 120                 125

Thr Lys His Ser Val Leu Gln Tyr Val Gly Gly Val Met Ser Val Glu
    130                 135                 140

Met Gln Ala Pro Lys Leu Leu Trp Leu Lys Glu Asn Leu Arg Glu Ile
145                 150                 155                 160

Cys Trp Asp Lys Ala Gly His Phe Phe Asp Leu Pro Asp Phe Leu Ser
                165                 170                 175

Trp Lys Ala Thr Gly Val Thr Ala Arg Ser Leu Cys Ser Leu Val Cys
```

```
                180             185             190
Lys Trp Thr Tyr Ser Ala Glu Lys Gly Trp Asp Asp Ser Phe Trp Lys
                195                 200                 205
Met Ile Gly Leu Glu Asp Phe Val Ala Asp Asn Tyr Ser Lys Ile Gly
                210                 215                 220
Asn Gln Val Leu Pro Pro Gly Ala Ser Leu Gly Asn Gly Leu Thr Pro
225                 230                 235                 240
Glu Ala Ala Arg Asp Leu Gly Leu Pro Gly Ile Ala Val Ala Ala
                245                 250                 255
Ser Leu Ile Asp Ala His Ala Gly Leu Gly Val Ile Gly Ala Asp
                260                 265                 270
Val Arg Gly His Gly Leu Ile Cys Glu Gly Gln Pro Val Thr Ser Arg
                275                 280                 285
Leu Ala Val Ile Cys Gly Thr Ser Ser Cys His Met Gly Ile Ser Lys
                290                 295                 300
Asp Pro Ile Phe Val Pro Gly Val Trp Gly Pro Tyr Phe Ser Ala Met
305                 310                 315                 320
Val Pro Gly Phe Trp Leu Asn Glu Gly Gly Gln Ser Val Thr Gly Lys
                325                 330                 335
Leu Ile Asp His Met Val Gln Gly His Ala Ala Phe Pro Glu Leu Gln
                340                 345                 350
Val Lys Ala Thr Ala Arg Cys Gln Ser Ile Tyr Ala Tyr Leu Asn Ser
                355                 360                 365
His Leu Asp Leu Ile Lys Lys Ala Gln Pro Val Gly Phe Leu Thr Val
                370                 375                 380
Asp Leu His Val Trp Pro Asp Phe His Gly Asn Arg Ser Pro Leu Ala
385                 390                 395                 400
Asp Leu Thr Leu Lys Gly Met Val Thr Gly Leu Lys Leu Ser Gln Asp
                405                 410                 415
Leu Asp Asp Leu Ala Ile Leu Tyr Leu Ala Thr Val Gln Ala Ile Ala
                420                 425                 430
Leu Gly Thr Arg Phe Ile Ile Glu Ala Met Glu Ala Ala Gly His Ser
                435                 440                 445
Ile Ser Thr Leu Phe Leu Cys Gly Gly Leu Ser Lys Asn Pro Leu Phe
450                 455                 460
Val Gln Met His Ala Asp Ile Thr Gly Met Pro Val Val Leu Ser Gln
465                 470                 475                 480
Glu Val Glu Ser Val Leu Val Gly Ala Ala Val Leu Gly Ala Cys Ala
                485                 490                 495
Ser Gly Asp Phe Ala Ser Val Gln Glu Ala Met Ala Lys Met Ser Lys
                500                 505                 510
Val Gly Lys Val Val Phe Pro Arg Leu Gln Asp Lys Lys Tyr Tyr Asp
                515                 520                 525
Lys Lys Tyr Gln Val Phe Leu Lys Leu Val Glu His Gln Lys Glu Tyr
                530                 535                 540
Leu Ala Ile Met Asn Asp Asp
545                 550
```

<210> SEQ ID NO 5
<211> LENGTH: 1665
<212> TYPE: DNA
<213> ORGANISM: Homo sapiens

<400> SEQUENCE: 5

-continued

```
aaattttgca tgatcgcatg agaatggat tttgttgctt tatctgatat tgtcctcagc    60
tcctcctgaa tttgccgaga tcttacagca gtcagtaagg tggaggaact gcaatgtctg   120
gtggagaaca gaaaccagag aggtactatg tgggtgtgga cgttggaaca ggcagtgtcc   180
gtgcagctct ggtggaccag agtggggtcc tgttggcttt gcagaccag ccaattaaga    240
attgggagcc ccagttcaac caccatgagc agtcctccga ggacatctgg gctgcgtgct   300
gtgttgtcac aaagaacttg agagagattt gctgggataa gcgggacat ttctttgatc    360
tcccggactt cttatcgtgg aaggcaacag tgtcacagc acggtctctc tgctccctgg    420
tgtgtaagtg gacatattca gcagagaaag gctgggacga cagtttctgg aaaatgattg   480
gtttggaaga ctttgttgca gataattaca gcaaaatagg aaaccaagtg ctacctcctg   540
gagcttctct tggaaatggg ctcacaccag aggcagcaag agaccttggc cttctccctg   600
ggattgcggt cgcagcttca ctcattgatg cccatgcagg aggactagga gtgattgggg   660
cagatgtgag agggcacggc ctcatctgtg aggggcagcc agtgacgtca cggctggctg   720
tcatctgtgg aacgtcttct tgtcacatgg ggatcagcaa agacccgatt tttgtaccag   780
gcgtctgggg gccttatttc tcagccatgg tacctgggtt ctggctgaat gaaggtggtc   840
agagcgttac tggaaaattg atagaccaca tggtacaagg ccatgctgct tttccagaac   900
tacaagtaaa ggccacagcc agatgccaga gtatatatgc atatttgaac agtcacctgg   960
atctgattaa gaaggctcag cctgtgggtt tccttactgt tgatttacat gtttggccaa  1020
atttccatgg caaccggtct cccttagcag atctgacact aaagggcatg gtcaccggat  1080
tgaaactgtc tcaggacctt gatgatcttg ccattctcta cctggccaca gttcaagcca  1140
ttgctttggg gactcgcttc attatagaag ccatggaggc agcagggcac tcaatcagta  1200
ctctttttcct atgtggaggc ctcagcaaga atccccttt tgtgcaaatg catgcggaca  1260
ttactggcat gcctgtggtc ctgtcgcaag aggtggagtc cgttcttgtg ggtgctgctg  1320
ttctgggtgc ctgtgcctca ggggatttcg cttctgtaca ggaagcaatg caaaaatga   1380
gcaaagttgg gaaagttgtg ttcccgagac tacaggataa aaatactat gataagaaat   1440
accaagtatt cctgaagctg gttgaacacc agaaggagta tttggcgatc atgaatgatg  1500
actgaacagg gcttgcaggt gctgatgcca gaagcttctg tgccattgca ttaaagactt  1560
gtcatttgat ccatgttcaa gacccttgag gtattgtttc atcatttctg tattgtcttt  1620
caataaagaa aacaaacatg tgcaaccaga aaaaaaaaaa aaaaa              1665
```

<210> SEQ ID NO 6
<211> LENGTH: 463
<212> TYPE: PRT
<213> ORGANISM: Homo sapiens

<400> SEQUENCE: 6

```
Met Ser Gly Gly Glu Gln Lys Pro Glu Arg Tyr Tyr Val Gly Val Asp
1               5                   10                  15

Val Gly Thr Gly Ser Val Arg Ala Ala Leu Val Asp Gln Ser Gly Val
            20                  25                  30

Leu Leu Ala Phe Ala Asp Gln Pro Ile Lys Asn Trp Glu Pro Gln Phe
        35                  40                  45

Asn His His Glu Gln Ser Ser Glu Asp Ile Trp Ala Ala Cys Cys Val
    50                  55                  60

Val Thr Lys Asn Leu Arg Glu Ile Cys Trp Asp Lys Ala Gly His Phe
65                  70                  75                  80
```

-continued

```
Phe Asp Leu Pro Asp Phe Leu Ser Trp Lys Ala Thr Gly Val Thr Ala
                 85                  90                  95
Arg Ser Leu Cys Ser Leu Val Cys Lys Trp Thr Tyr Ser Ala Glu Lys
            100                 105                 110
Gly Trp Asp Asp Ser Phe Trp Lys Met Ile Gly Leu Glu Asp Phe Val
            115                 120                 125
Ala Asp Asn Tyr Ser Lys Ile Gly Asn Gln Val Leu Pro Pro Gly Ala
        130                 135                 140
Ser Leu Gly Asn Gly Leu Thr Pro Glu Ala Ala Arg Asp Leu Gly Leu
145                 150                 155                 160
Leu Pro Gly Ile Ala Val Ala Ala Ser Leu Ile Asp Ala His Ala Gly
                165                 170                 175
Gly Leu Gly Val Ile Gly Ala Asp Val Arg Gly His Gly Leu Ile Cys
            180                 185                 190
Glu Gly Gln Pro Val Thr Ser Arg Leu Ala Val Ile Cys Gly Thr Ser
            195                 200                 205
Ser Cys His Met Gly Ile Ser Lys Asp Pro Ile Phe Val Pro Gly Val
        210                 215                 220
Trp Gly Pro Tyr Phe Ser Ala Met Val Pro Gly Phe Trp Leu Asn Glu
225                 230                 235                 240
Gly Gly Gln Ser Val Thr Gly Lys Leu Ile Asp His Met Val Gln Gly
                245                 250                 255
His Ala Ala Phe Pro Glu Leu Gln Val Lys Ala Thr Ala Arg Cys Gln
            260                 265                 270
Ser Ile Tyr Ala Tyr Leu Asn Ser His Leu Asp Leu Ile Lys Lys Ala
        275                 280                 285
Gln Pro Val Gly Phe Leu Thr Val Asp Leu His Val Trp Pro Asp Phe
        290                 295                 300
His Gly Asn Arg Ser Pro Leu Ala Asp Leu Thr Leu Lys Gly Met Val
305                 310                 315                 320
Thr Gly Leu Lys Leu Ser Gln Asp Leu Asp Leu Ala Ile Leu Tyr
                325                 330                 335
Leu Ala Thr Val Gln Ala Ile Ala Leu Gly Thr Arg Phe Ile Ile Glu
            340                 345                 350
Ala Met Glu Ala Ala Gly His Ser Ile Ser Thr Leu Phe Leu Cys Gly
            355                 360                 365
Gly Leu Ser Lys Asn Pro Leu Phe Val Gln Met His Ala Asp Ile Thr
        370                 375                 380
Gly Met Pro Val Val Leu Ser Gln Glu Val Glu Ser Val Leu Val Gly
385                 390                 395                 400
Ala Ala Val Leu Gly Ala Cys Ala Ser Gly Asp Phe Ala Ser Val Gln
                405                 410                 415
Glu Ala Met Ala Lys Met Ser Lys Val Gly Lys Val Val Phe Pro Arg
            420                 425                 430
Leu Gln Asp Lys Lys Tyr Tyr Asp Lys Lys Tyr Gln Val Phe Leu Lys
        435                 440                 445
Leu Val Glu His Gln Lys Glu Tyr Leu Ala Ile Met Asn Asp Asp
450                 455                 460
```